United States Patent [19]

Boden

[11] 4,336,164

[45] Jun. 22, 1982

[54] BRANCHED CHAIN OLEFINIC ALCOHOLS USEFUL IN PERFUME COMPOSITIONS

[75] Inventor: Richard M. Boden, Monmouth Beach, N.J.

[73] Assignee: International Flavors & Fragrances Inc., New York, N.Y.

[21] Appl. No.: 252,134

[22] Filed: Apr. 9, 1981

Related U.S. Application Data

[63] Continuation-in-part of Ser. No. 212,887, Dec. 4, 1980, Pat. No. 4,318,934.

[51] Int. Cl.$^3$ .......................... A61K 7/46; C11B 9/00
[52] U.S. Cl. .............................. 252/522 R; 131/276; 252/174.11; 568/875
[58] Field of Search ...................... 252/522 R; 568/875

[56] References Cited

U.S. PATENT DOCUMENTS

| | | | |
|---|---|---|---|
| 3,075,003 | 1/1963 | Blumenthal | 568/875 |
| 3,296,080 | 1/1967 | Meuly et al. | 252/522 R |
| 4,066,710 | 1/1978 | Ochsner | 568/875 |
| 4,073,813 | 2/1978 | Cordier | 568/875 |
| 4,303,555 | 12/1981 | Boden | 252/522 R |

OTHER PUBLICATIONS

Actander, S., "Perfume and Flavor Chemicals", pub. author, (1969), vols. I and II, Monographs 960, 964, 1803.

Primary Examiner—John F. Niebling
Attorney, Agent, or Firm—Arthur L. Liberman

[57] ABSTRACT

Described is the novel compound genus defined according to the structure:

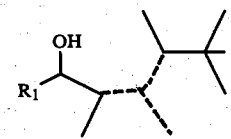

wherein $R_1$ is selected from the group consisting of methyl and isopropyl alcohol and wherein the dashed lines represents a carbon-carbon double bond and each of the other of the dashed lines represent carbon-carbon single bonds useful in augmenting or enhancing the aroma or taste of consumable materials including perfumes, colognes, perfumed articles (including solid or liquid anionic, cationic, nonionic or zwitterionic detergents) smoking tobacco or smoking tobacco articles.

2 Claims, 33 Drawing Figures

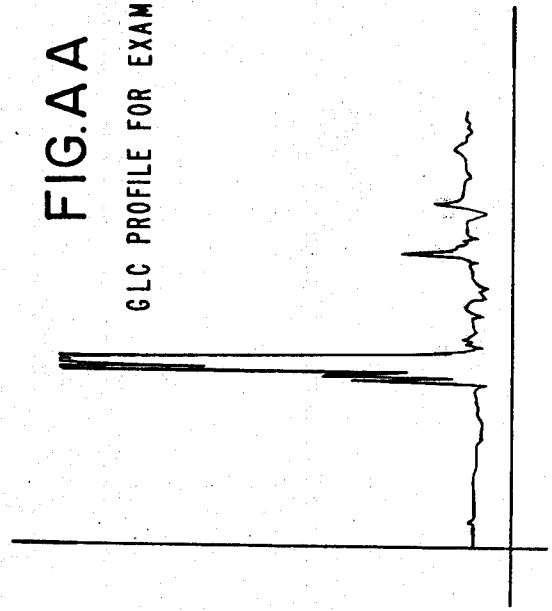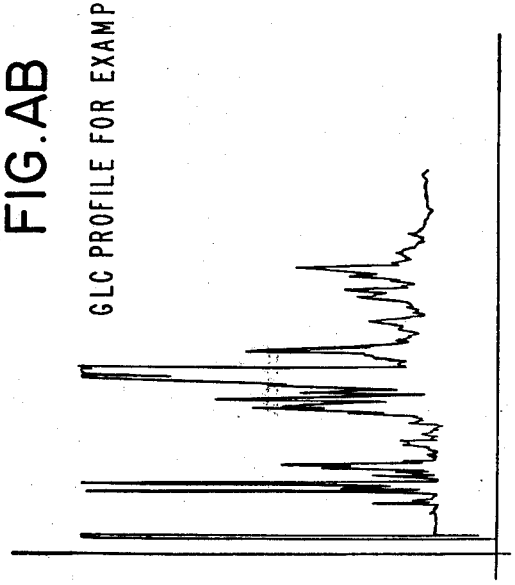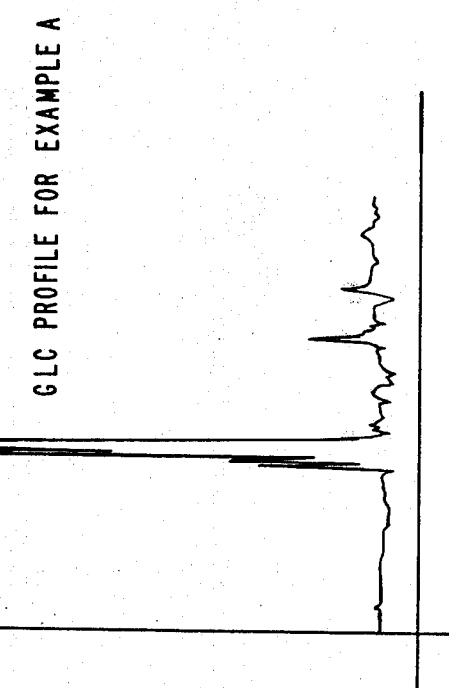

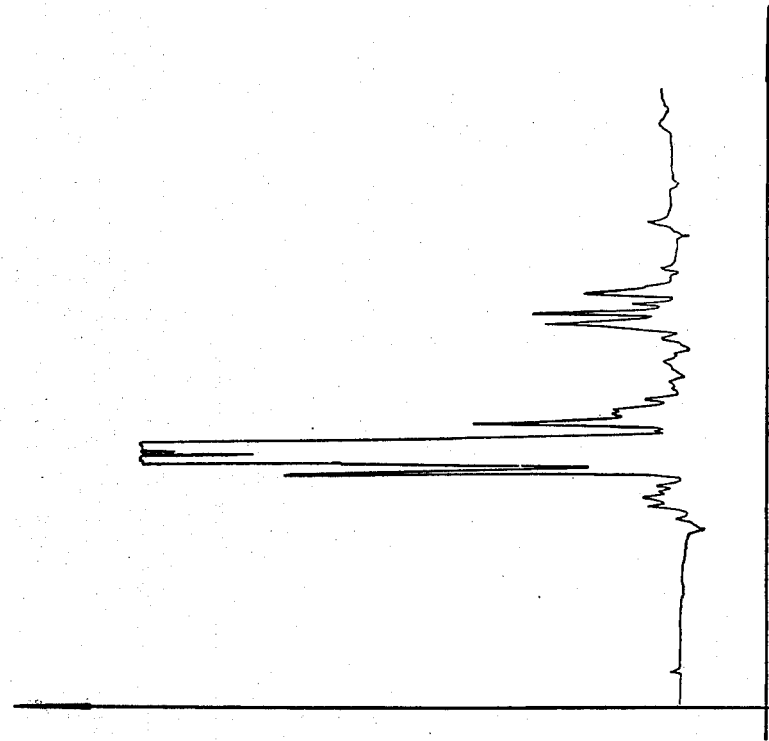
FIG.AD
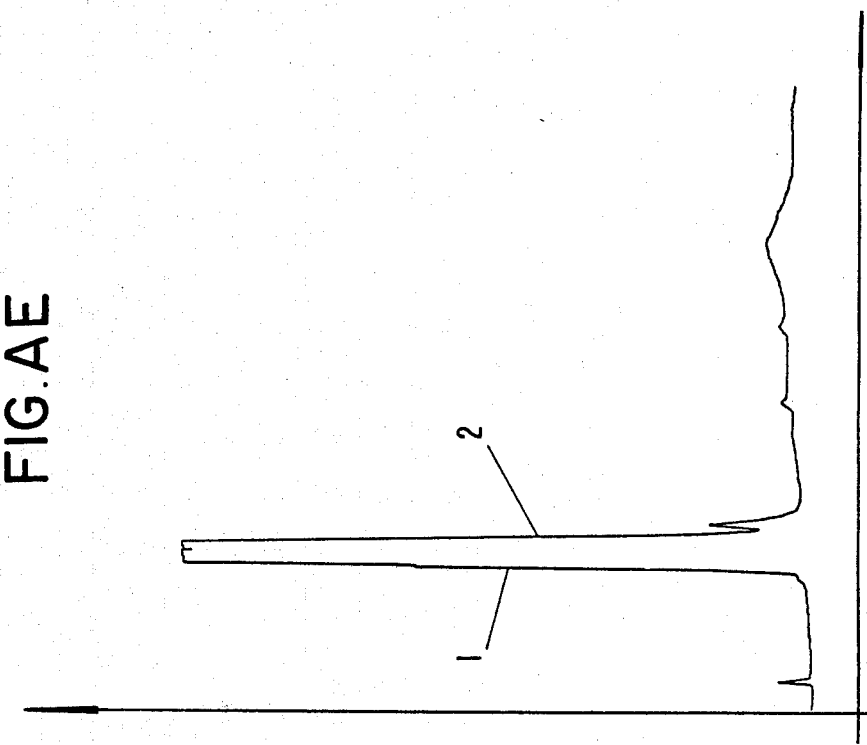
FIG.AE

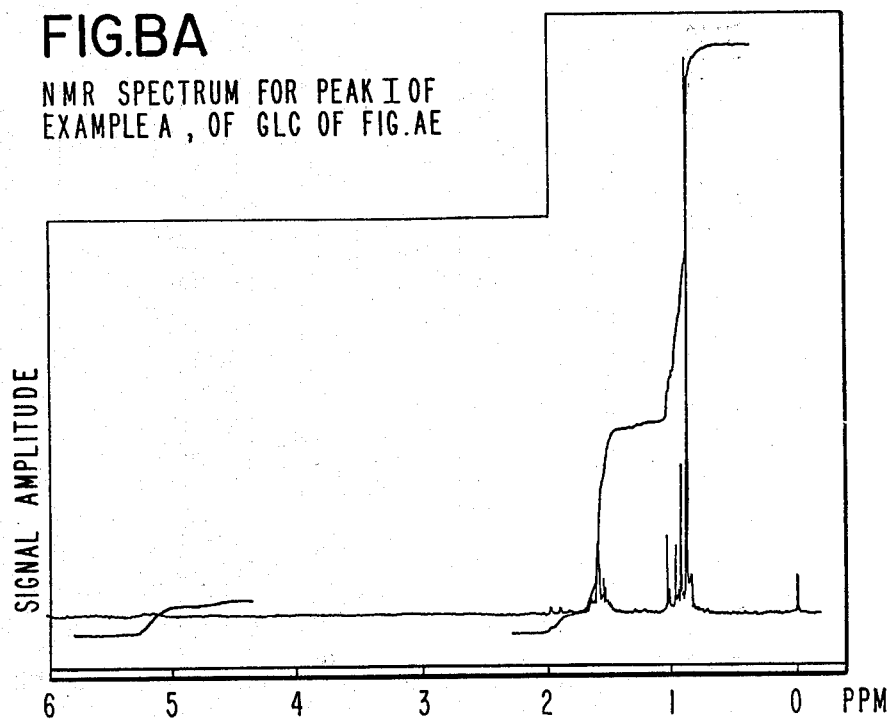
FIG.BA
NMR SPECTRUM FOR PEAK I OF EXAMPLE A, OF GLC OF FIG.AE
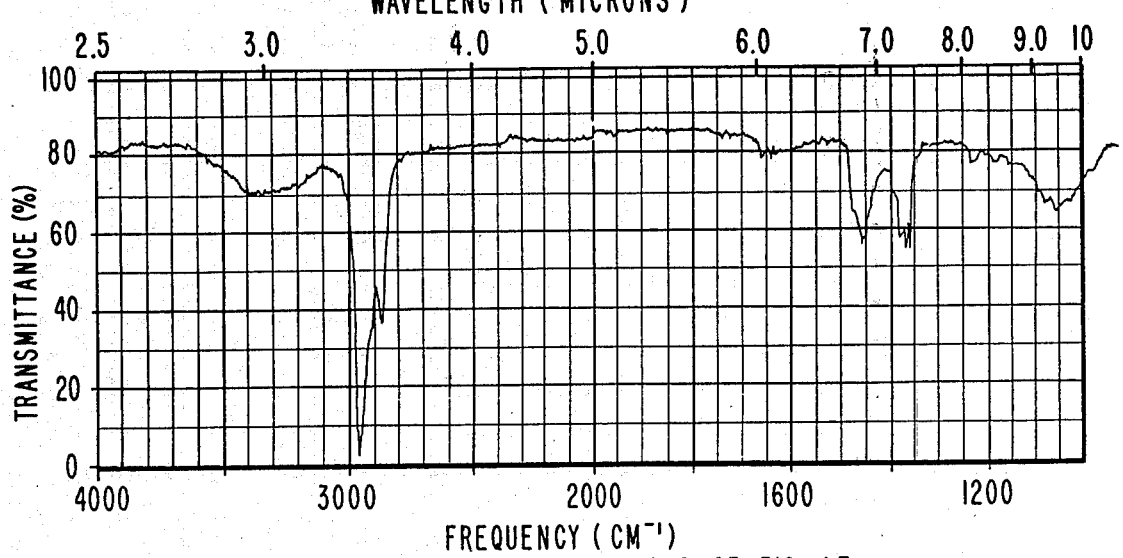
IR SPECTRUM FOR EXAMPLE A, PEAK I, OF GLC OF FIG.AE.
FIG.BB

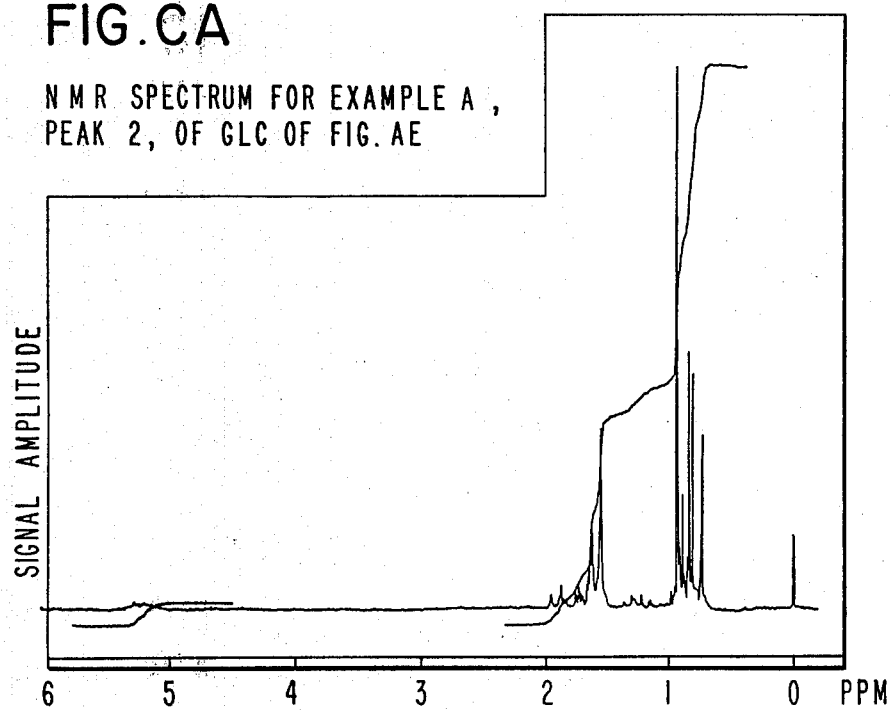
FIG.CA
NMR SPECTRUM FOR EXAMPLE A, PEAK 2, OF GLC OF FIG.AE
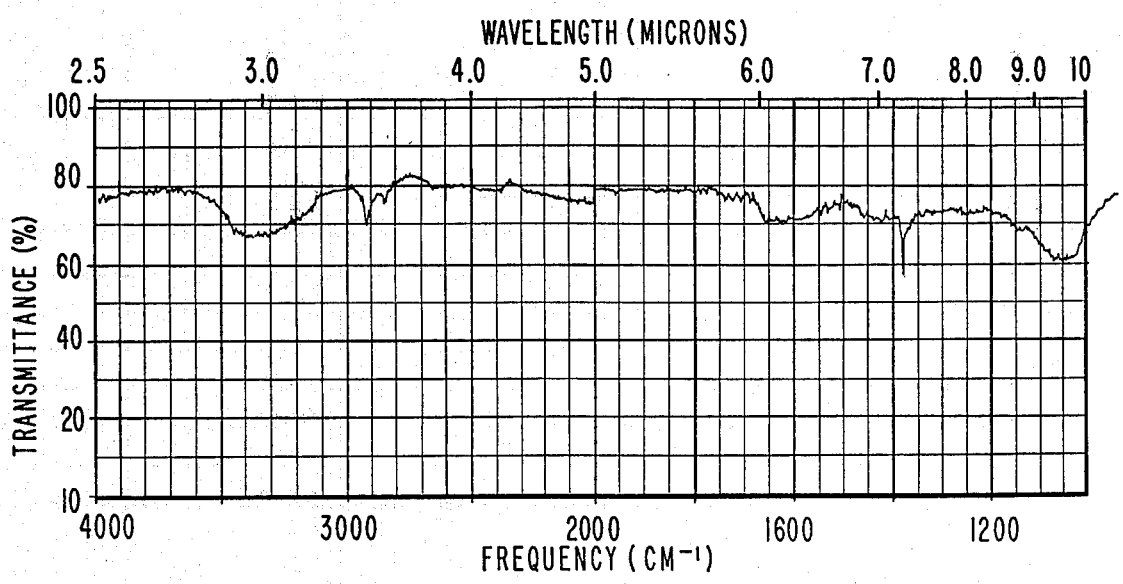
IR SPECTRUM FOR EXAMPLE I, PEAK 2 OF GLC OF FIG.AE
FIG.CB

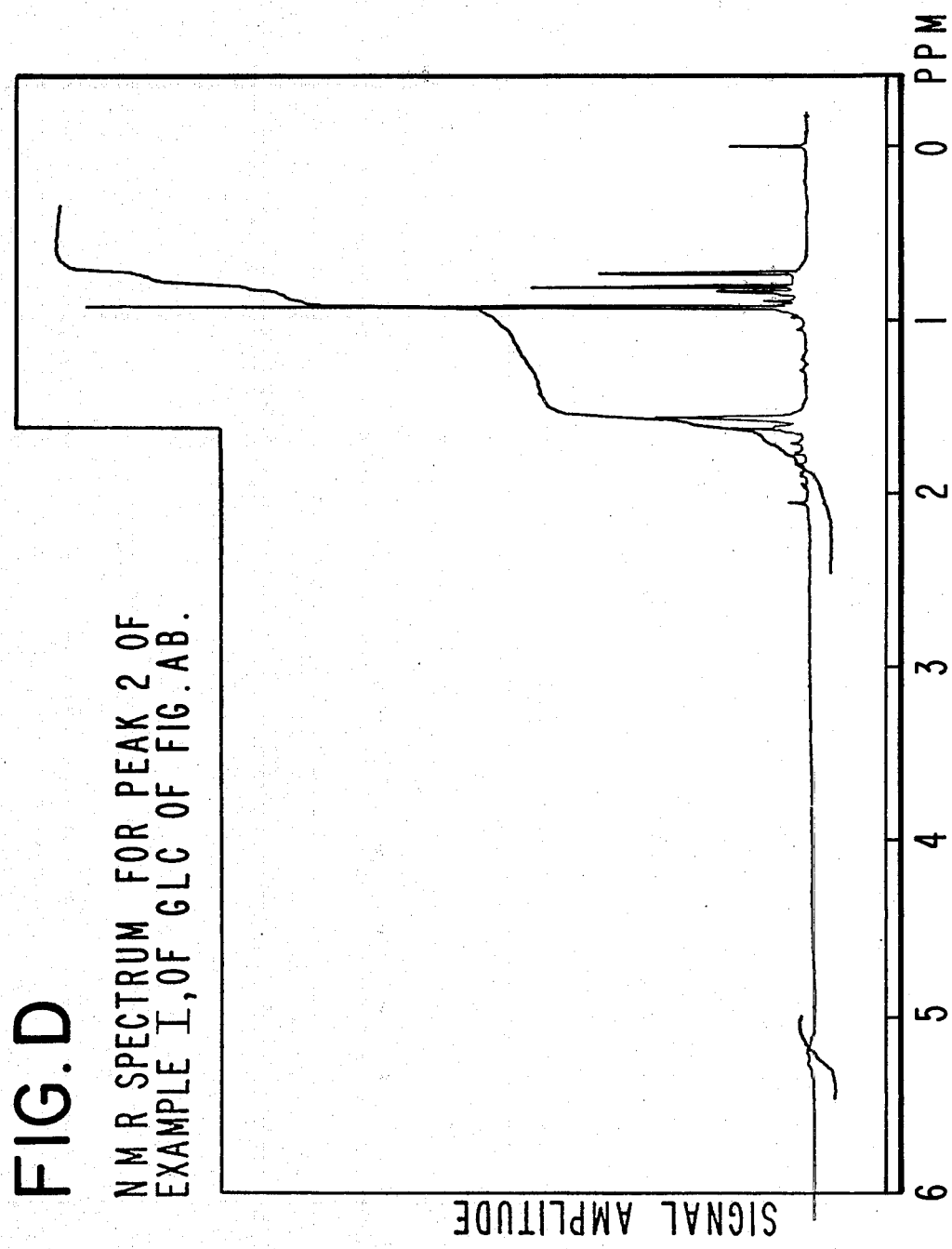
FIG. D
NMR SPECTRUM FOR PEAK 2 OF EXAMPLE I, OF GLC OF FIG. AB.

GLC PROFILE FOR EXAMPLE I.

IR SPECTRUM FOR PEAK 3 OF EXAMPLE I.

FIG. 2B

IR SPECTRUM FOR PEAK 4 OF EXAMPLE I.

FIG. 2C

IR SPECTRUM FOR PEAK 5 OF EXAMPLE I.

IR SPECTRUM FOR PEAK 6 OF EXAMPLE I.

IR SPECTRUM FOR PEAK 7 OF EXAMPLE I.

IR SPECTRUM FOR PEAK 8 OF EXAMPLE I.

IR SPECTRUM FOR PEAK 9 OF EXAMPLE I.

IR SPECTRUM FOR PEAK 10 OF EXAMPLE I.

NMR SPECTRUM FOR EXAMPLE I.

NMR SPECTRUM FOR EXAMPLE I.

NMR SPECTRUM FOR EXAMPLE I

FIG.3
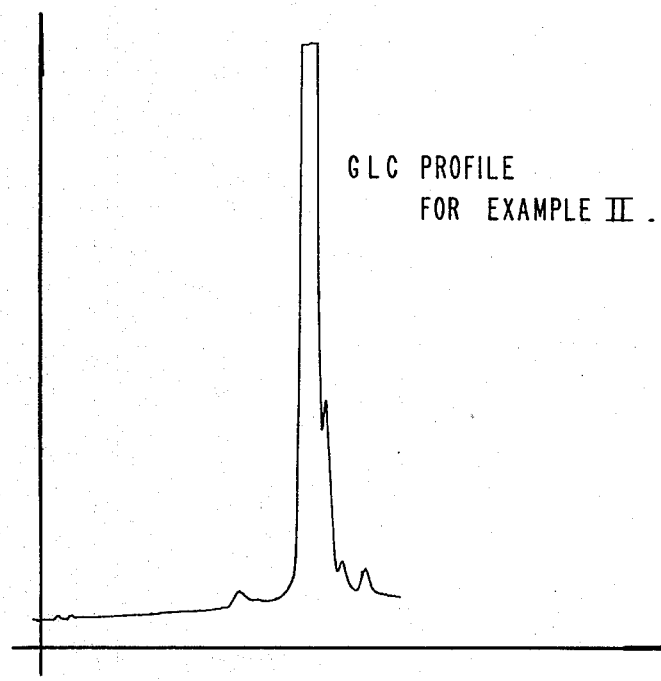
GLC PROFILE FOR EXAMPLE II.
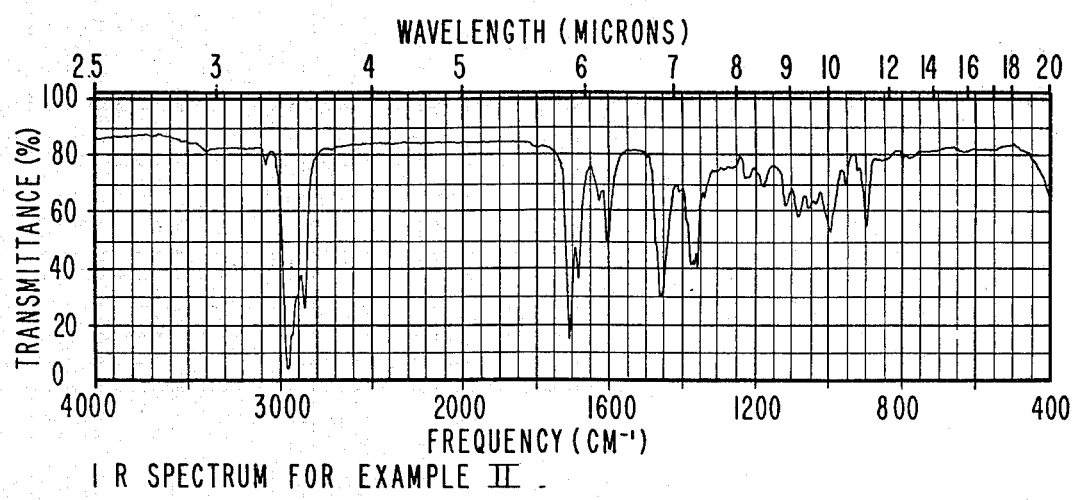
IR SPECTRUM FOR EXAMPLE II.
FIG.4

FIG.5
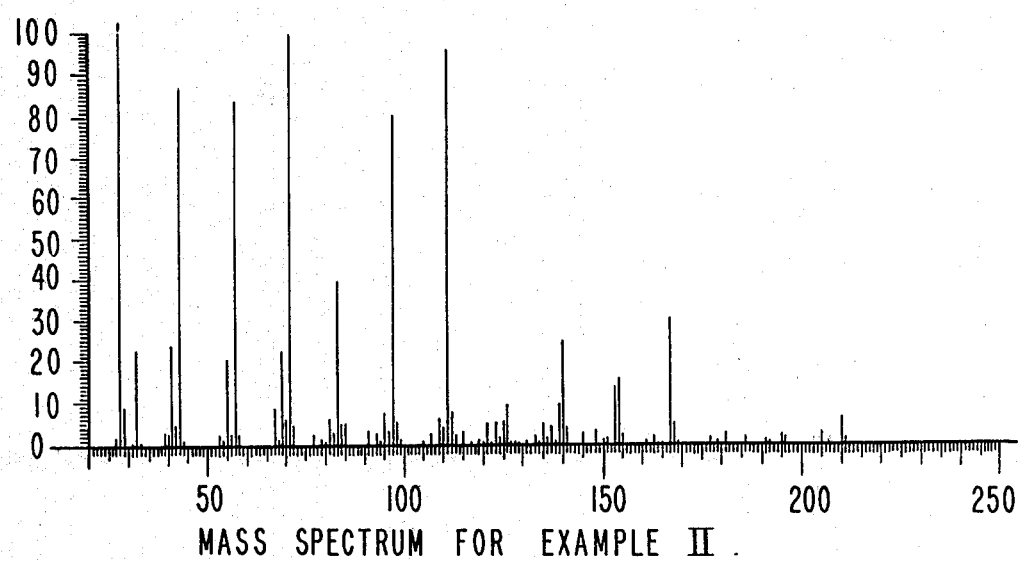
MASS SPECTRUM FOR EXAMPLE II.
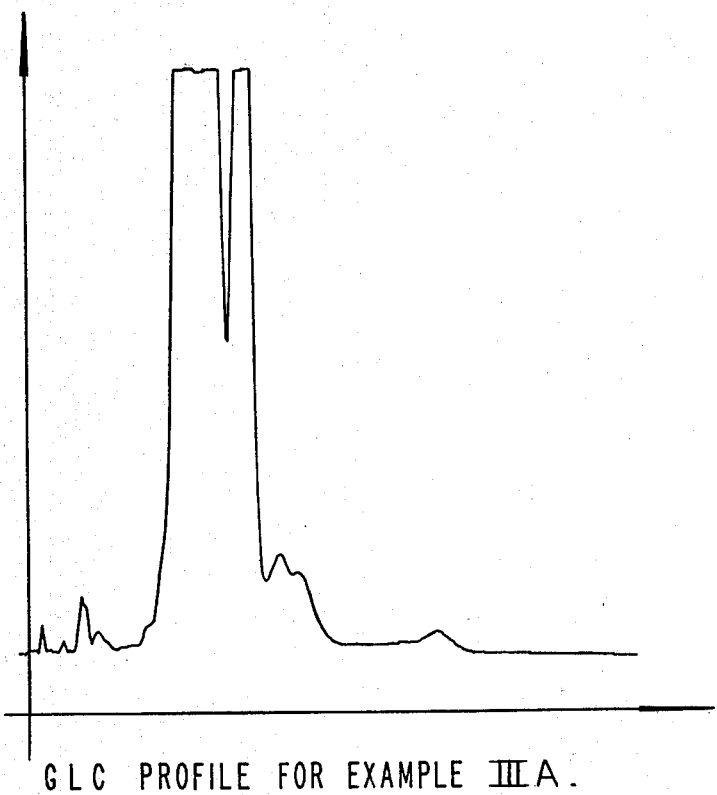
GLC PROFILE FOR EXAMPLE IIIA.
FIG.6

GLC PROFILE FOR EXAMPLE III B

GLC PROFILE FOR EXAMPLE IV A.

GLC PROFILE FOR EXAMPLE V.

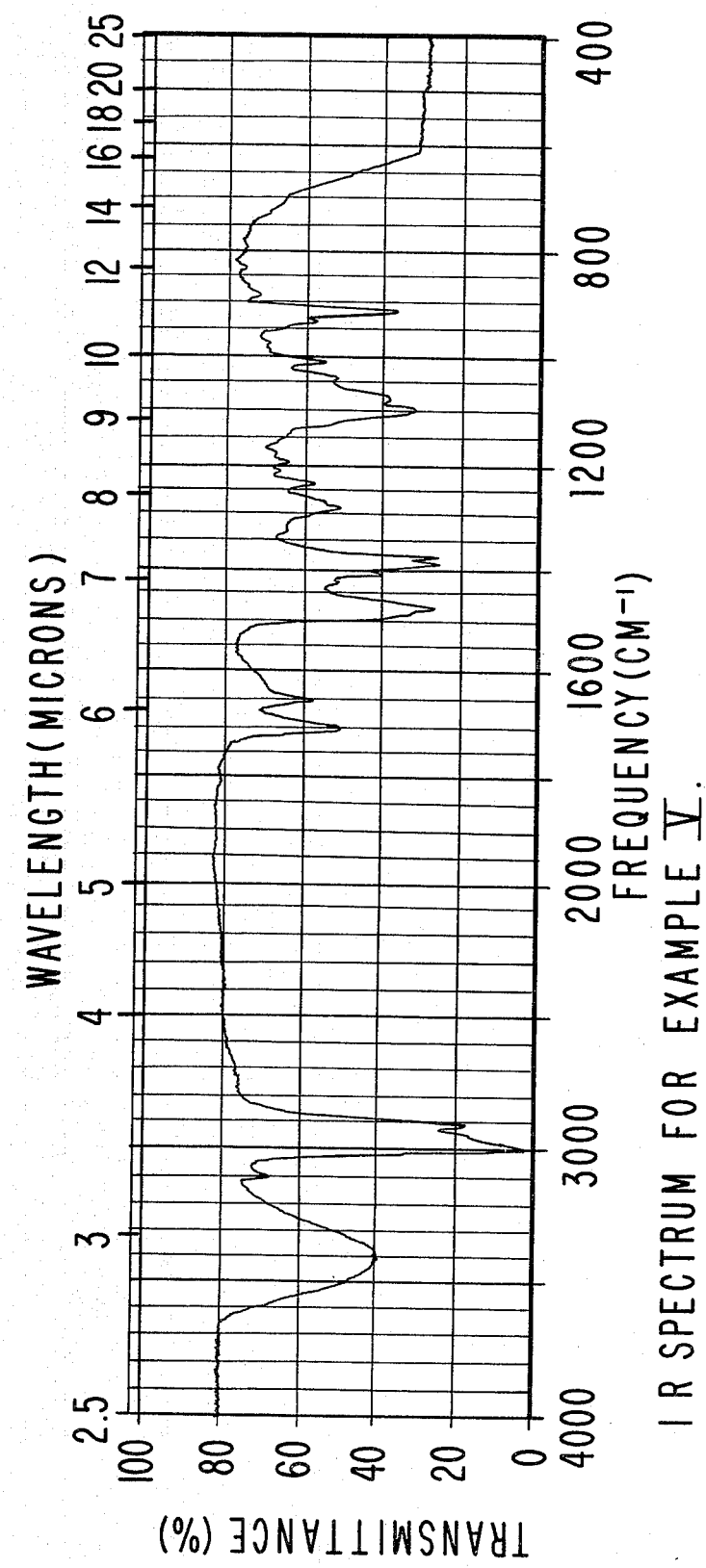

FIG. II
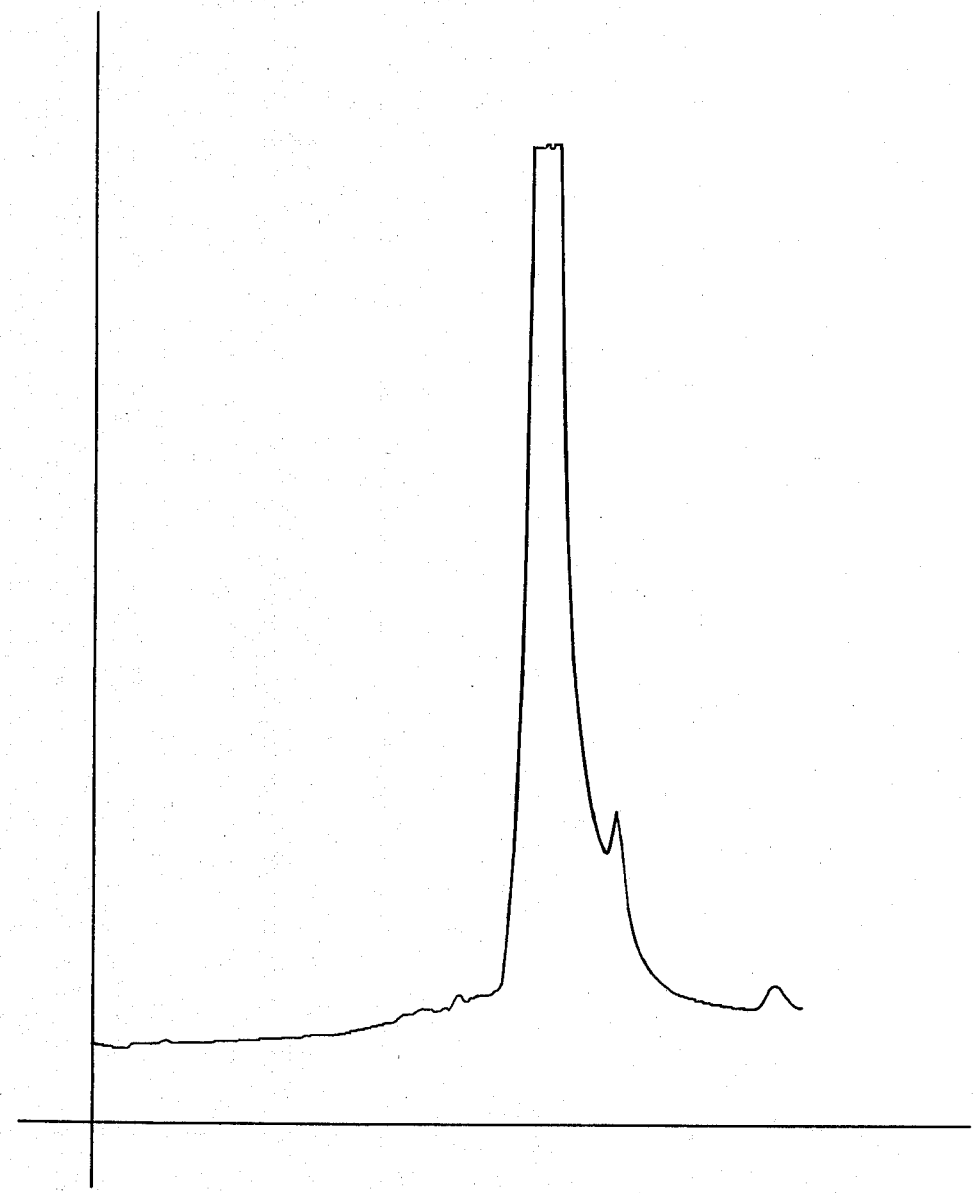
GLC PROFILE FOR FRACTION 4 OF EXAMPLE VI.

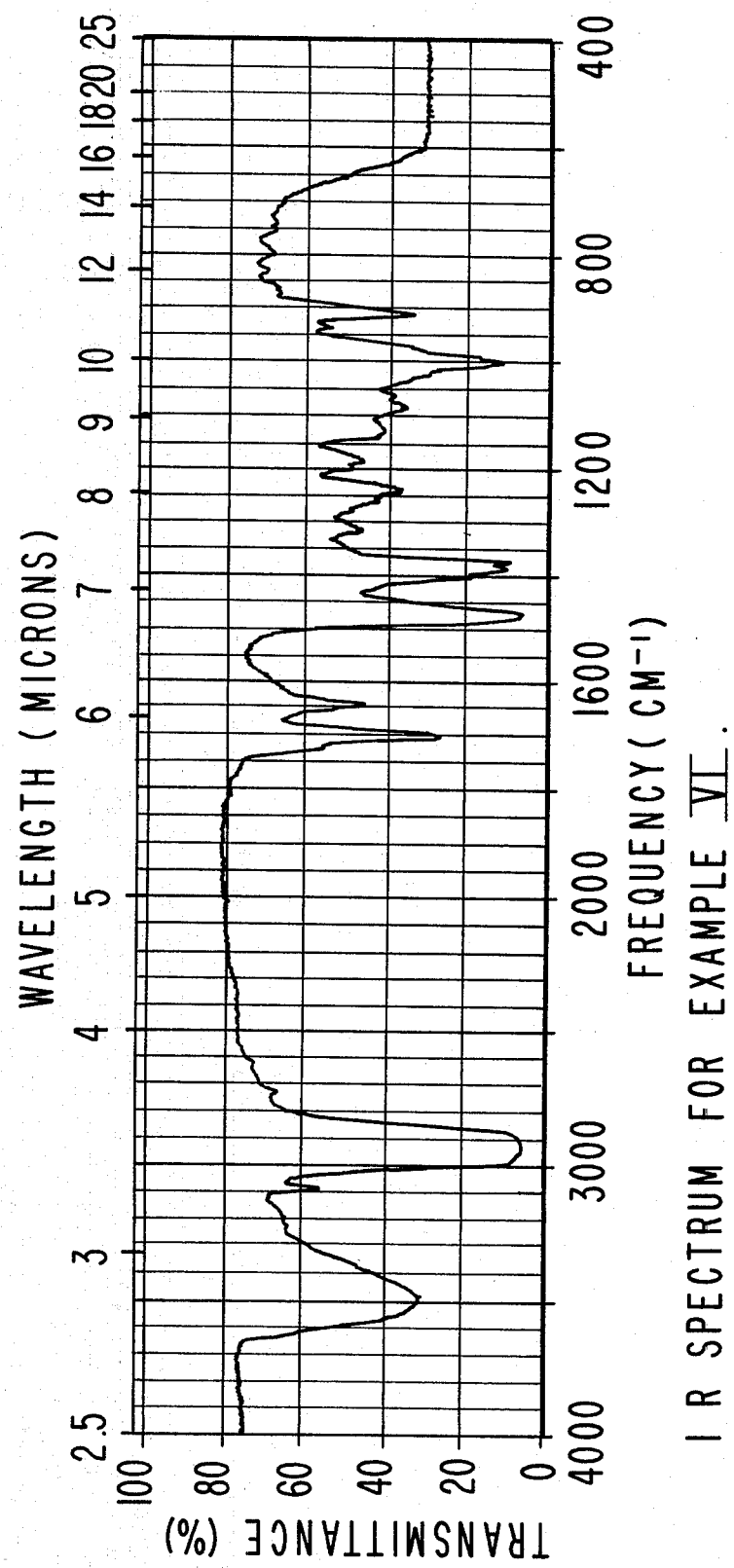

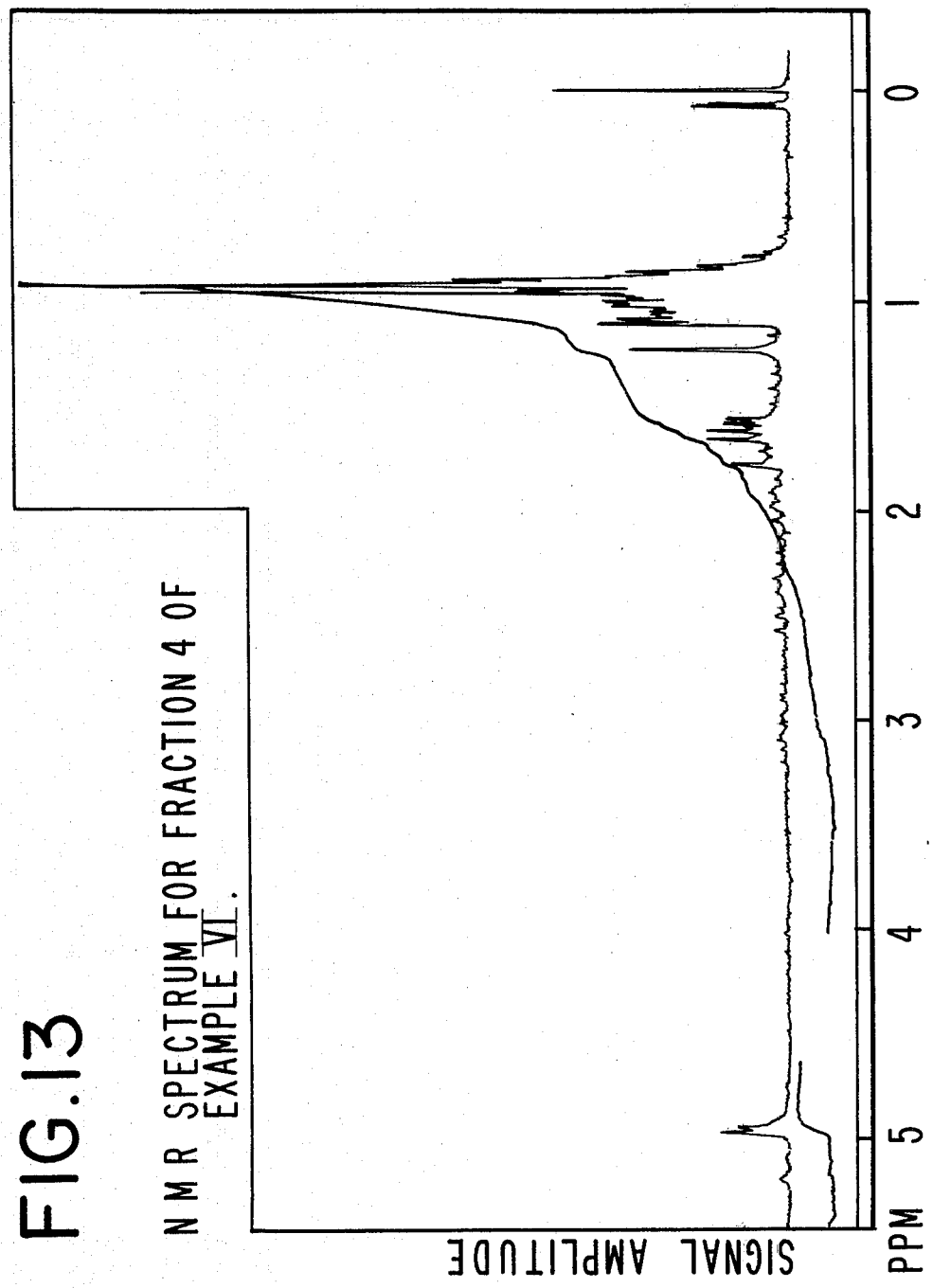
FIG.13 NMR SPECTRUM FOR FRACTION 4 OF EXAMPLE VI.

BRANCHED CHAIN OLEFINIC ALCOHOLS USEFUL IN PERFUME COMPOSITIONS

This Application is a Continuation-in-Part of Application for U.S. Leters Patent Ser. No. 212,887, filed on Dec. 4, 1980, Pat. No. 4,318,934.

BACKGROUND OF THE INVENTION

Materials which can provide amber, woody and fruity aroma profiles with vetiver-like topnotes particularly those materials which are relatively inexpensive are highly sought after in the art of perfumery. Many of the natural materials which provide such fragrance profiles and contribute desired nuances to perfumery compositions and perfumed article substances are high in cost, vary in quality from one batch to another and-/or are generally subject to the usual variations of natural products.

There is, accordingly, a continuing effort to find synthetic materials which will replace the essential fragrance notes provided by natural essential oils or compositions thereof. Unfortunately, many of these synthetic materials either have the desired nuances only to a relatively small degree or else contribute undesirable or unwanted odor to the composition. The search for materials which can provide a more refined amber, woody, fruity and vetiver-like aroma has been difficult and relatively costly in the areas of both natural products and synthetic products.

Materials which can provide woody, oriental and minty aroma and taste profiles both prior to and on smoking in the mainstream and the sidestream of smoking tobacco articles are desirable for augmenting or enhancing the aroma and taste of smoking tobacco and smoking tobacco articles, e.g. cigarettes and cigars.

Even more desirable is a product that can serve to substitute for difficult-to-obtain natural perfumery oils and expensive synthetic ingredients of perfume compositions and, at the same time, substitute for expensive flavoring ingredients in smoking tobacco and in smoking tobacco articles.

Perfumery materials which are inexpensive such as dihydro linalool(3,7-dimethyl-6-octen-3-ol) and dihydro myrcenol(3-methylene-7-methyloctanol-7) do not provide the vetiver-like fragrance profiles that are provided by the more expensive, more complex molecules such as vetivone.

Dihydro linalool according to "Perfume and Flavor Chemicals (Aroma Chemicals)" by Steffen Arctander (1969) having the Structure:

```
            CH3
             |  OH
             | /
             C
           /   \
        H2C     CH2
         |       |
        H2C     CH3
           \
            CH
             |
            C(CH3)2
``` at Monograph 960 is indicated to have a fresh, floral, citrusy aroma which is less woody than linalool and more powerful and more lime-like than tetrahydro linalool. On the other hand, dihydro myrcenol having the structure:

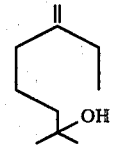

(at number 964 of Arctander) is described as being powerful, fresh lime-like overall citrusy, floral and sweet with little or no terpenic undertones. Dihydro myrcenyl acetate described at Monograph 965 of Arctander having the structure:

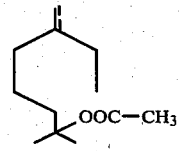

is described as sweet, spicy, herbaceous, fresh and somewhat fruity with a bergamot-like character but poor tenacity.

The chemicals described in the prior art such as dihydro myrcenyl acetate, dihydro myrcenol or dihydro linalool have aroma profiles or chemical structures which are not even remotely similar to the compounds of our invention.

BRIEF DESCRIPTION OF THE DRAWINGS

FIG. AA represents the GLC profile for the reaction product of Example A using a 70% sulfuric acid catalyst at 35% C.

FIG. AB represents the GLC profile for the reaction product of Example A using an Amberlyst ® 15 acidic ion exchange resin catalyst at a temperature of 150° C.

FIG. AC represents the GLC profile for the reaction product of Example A, using an Amberlyst ® 15 catalyst at 100° C.

FIG. AD represents the GLC profile for the reaction product of Example A, using a sulfuric acid catalyst and an alpha-methylstyrene diluent at 35° C. according to the conditions of United Kingdom Patent Specification 796,130 (crude reaction product).

FIG. AE represents the GLC profile for the reaction product of Example I, using a sulfuric acid catalyst, at 35° C. and an alpha-methyl styrene diluent according to the conditions of United Kingdom Patent Specification 796,130 (distilled reaction product).

FIG. BA represents the NMR spectrum for Peak 1 of the GLC profile of FIG. AE.

FIG. BB represents the infra-red spectrum for Peak 1 of the GLC profile of FIG. AE.

FIG. CA represents the NMR spectrum fir Peak 2 of the GLC profile of FIG. AE.

FIG. CB represents the infra-red spectrum for Peak 2 of the GLC profile of FIG. AE.

FIG. D represents the NMR spectrum for Peak 2 of the GLC profile of FIG. AB.

Figure 1:
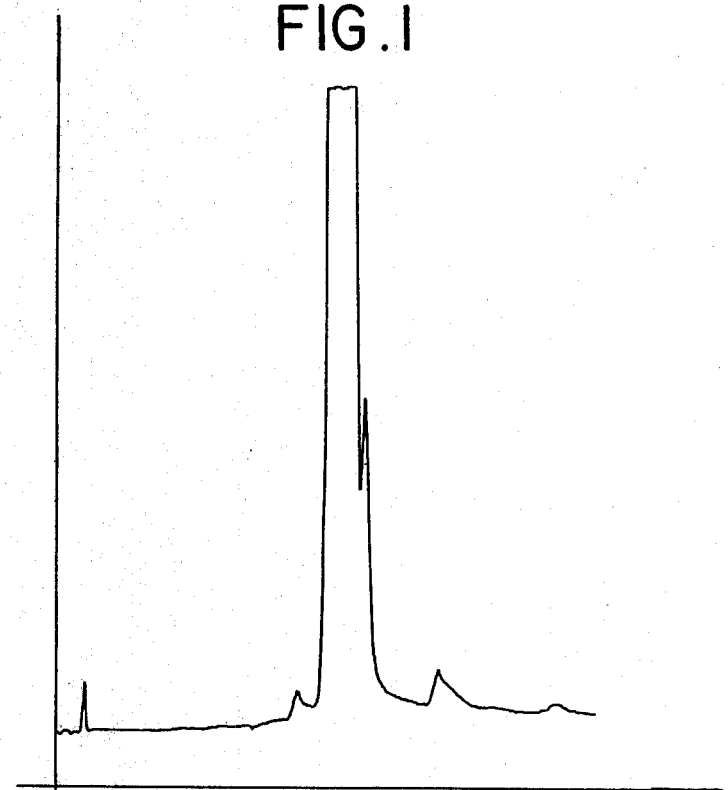

FIG. 1 sets forth the GLC profile for the reaction product of Example I, containing compounds defined according to the structure:

wherein in each molecule of the mixture, one of the dashed lines is a carbon-carbon double bond and the other of the dashed lines are carbon-carbon single bonds.

Figure 2A:
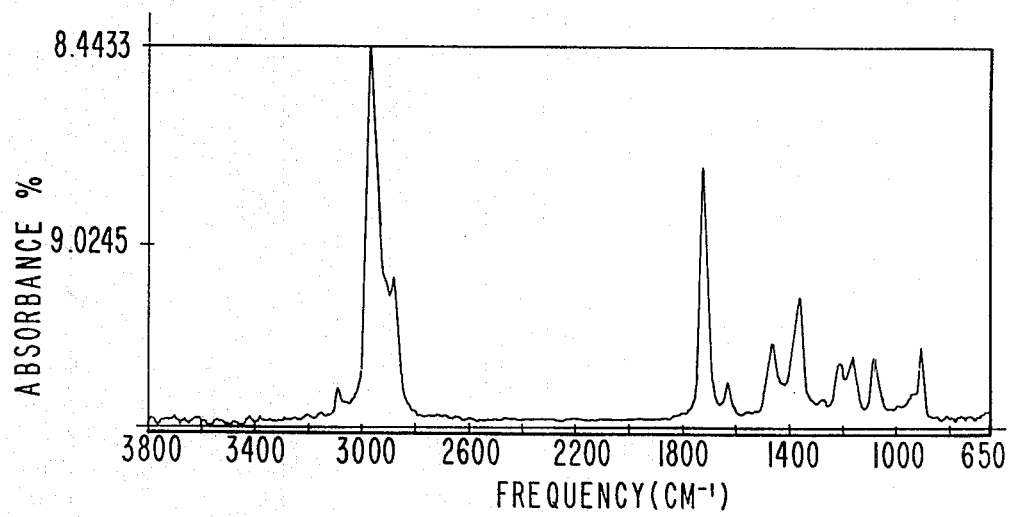

FIG. 2A represents the infra-red spectrum of Peak 3 of the GLC profile of FIG. 1.

FIG. 2B represents the infra-red spectrum of Peak 4 of the GLC profile of FIG. 1.

FIG. 2C represents the infra-red spectrum for Peak 5 of the GLC profile of FIG. 1.

Figure 2D:
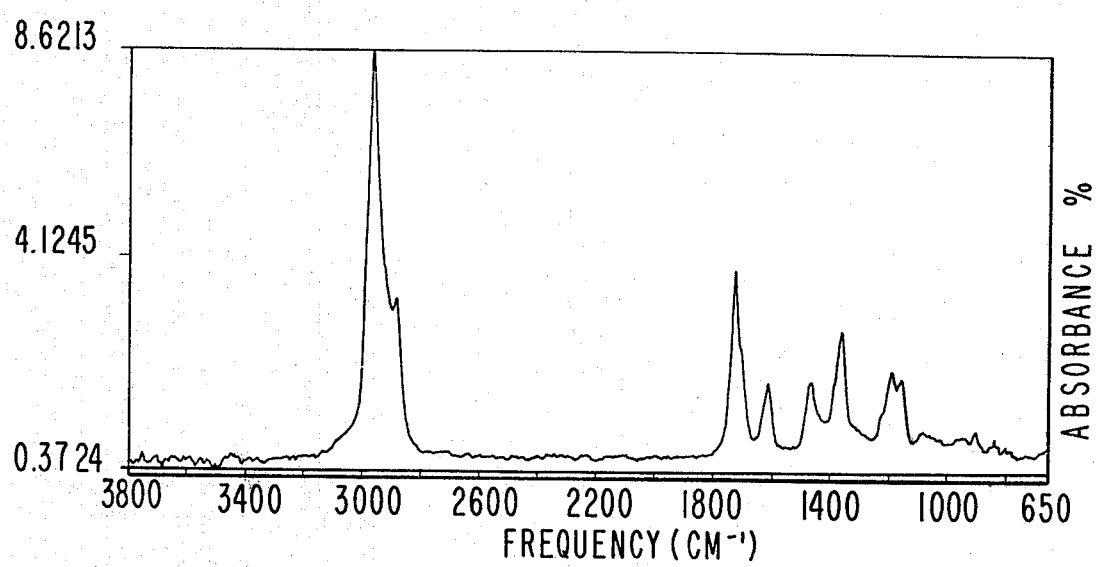

FIG. 2D represents the infra-red spectrum for Peak 6 of the GLC profile of FIG. 1.

Figure 2E:
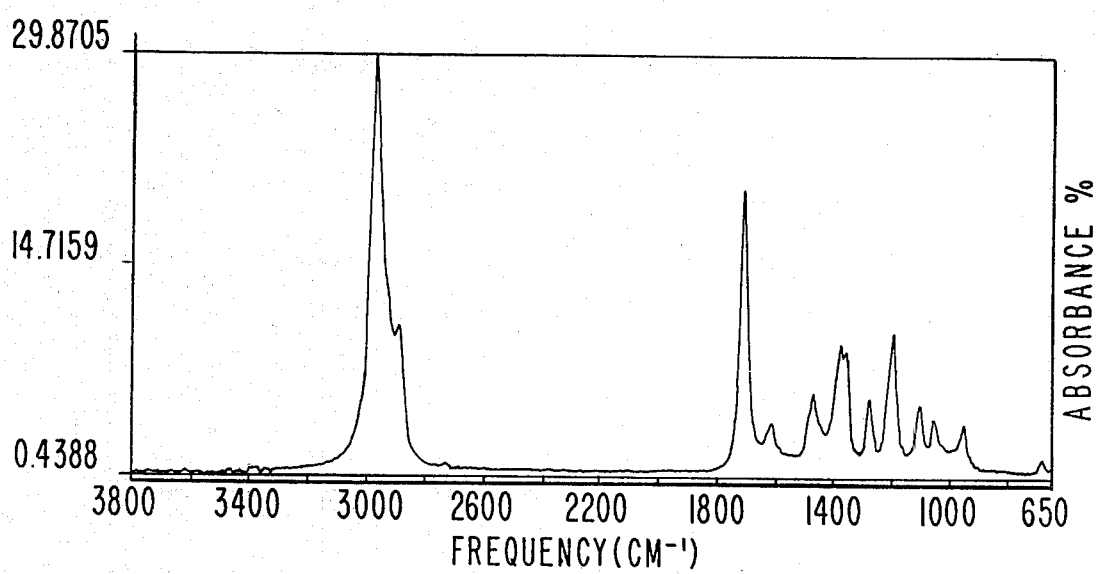

FIG. 2E represents the infra-red spectrum for Peak 7 of the GLC profile of FIG. 1.

Figure 2F:
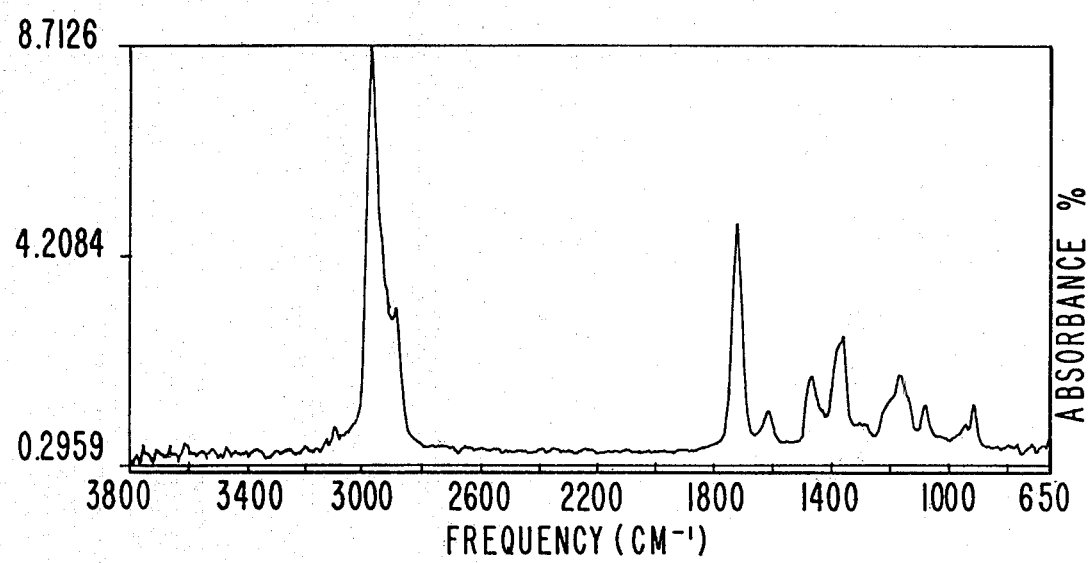

FIG. 2F represents the infra-red spectrum for Peak 8 of the GLC profile of FIG. 1.

Figure 2G:
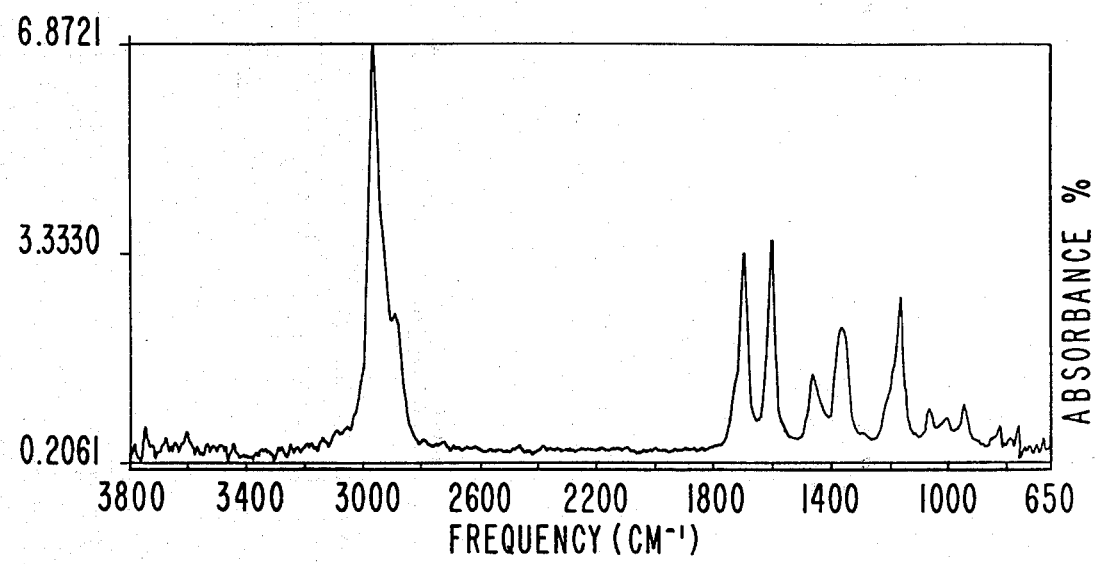

FIG. 2G represents the infra-red spectrum for Peak 9 of the GLC profile of FIG. 1.

Figure 2H:
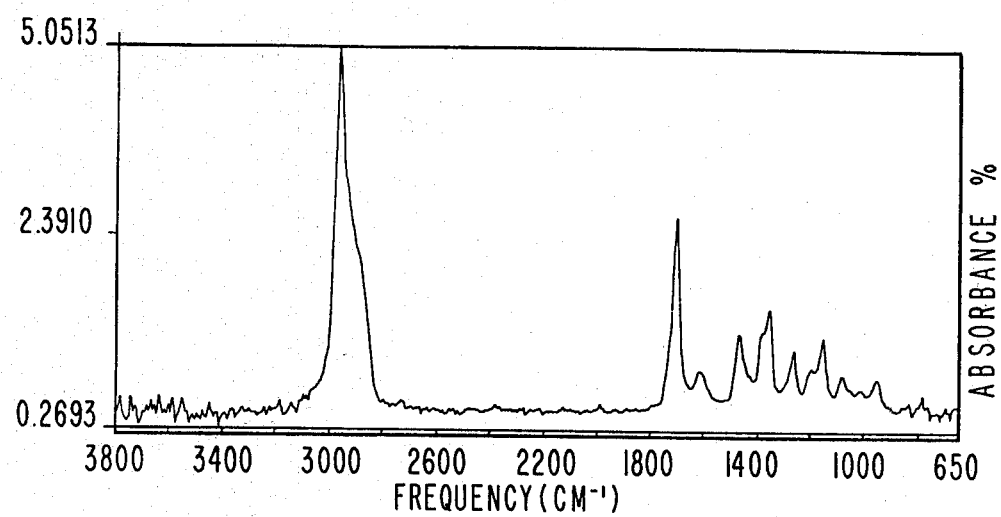

FIG. 2H represents the infra-red spectrum of Peak 10 of the GLC profile of FIG. 1.

Figure 2J:
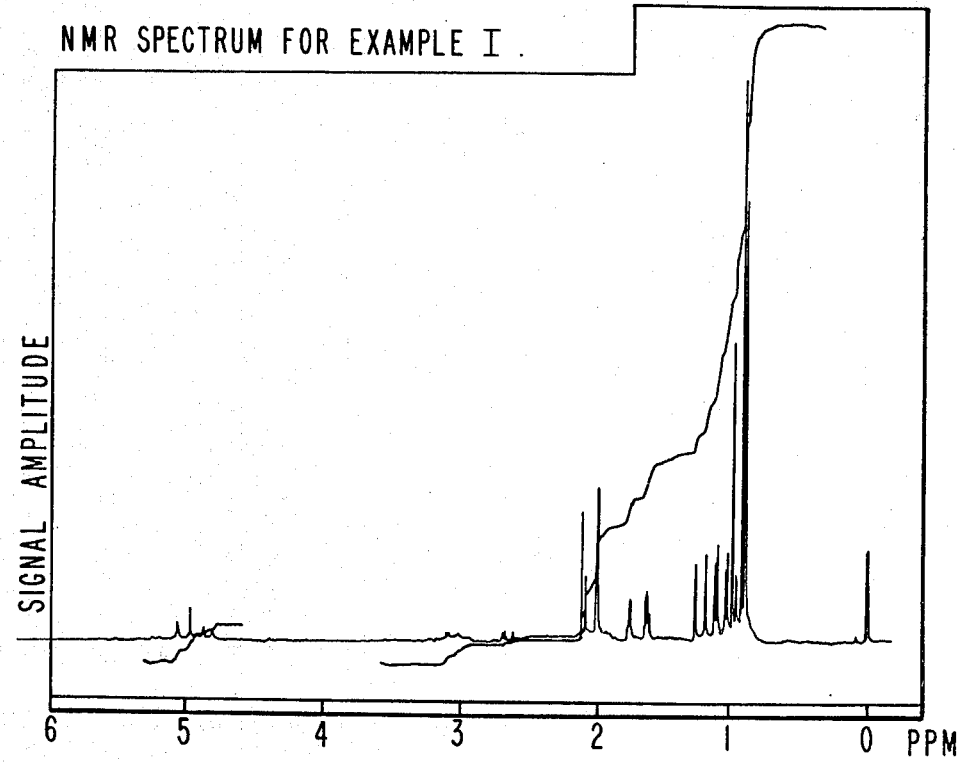

FIG. 2J represents the NMR spectrum for a mixture of compounds having the structues:

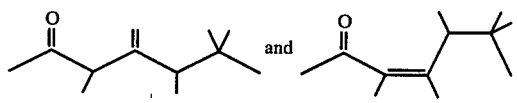

produced according to Example I.

Figure 2K:
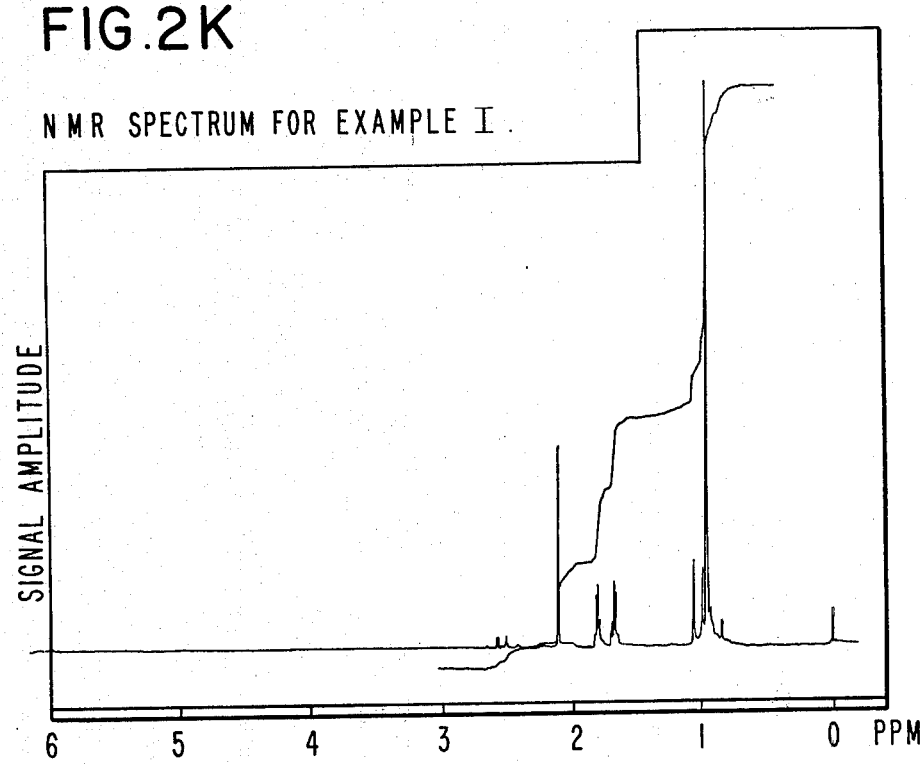

FIG. 2K represents the NMR spectrum for the compound having the structure:

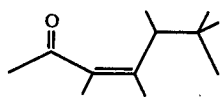

produced according to Example I.

Figure 2L:
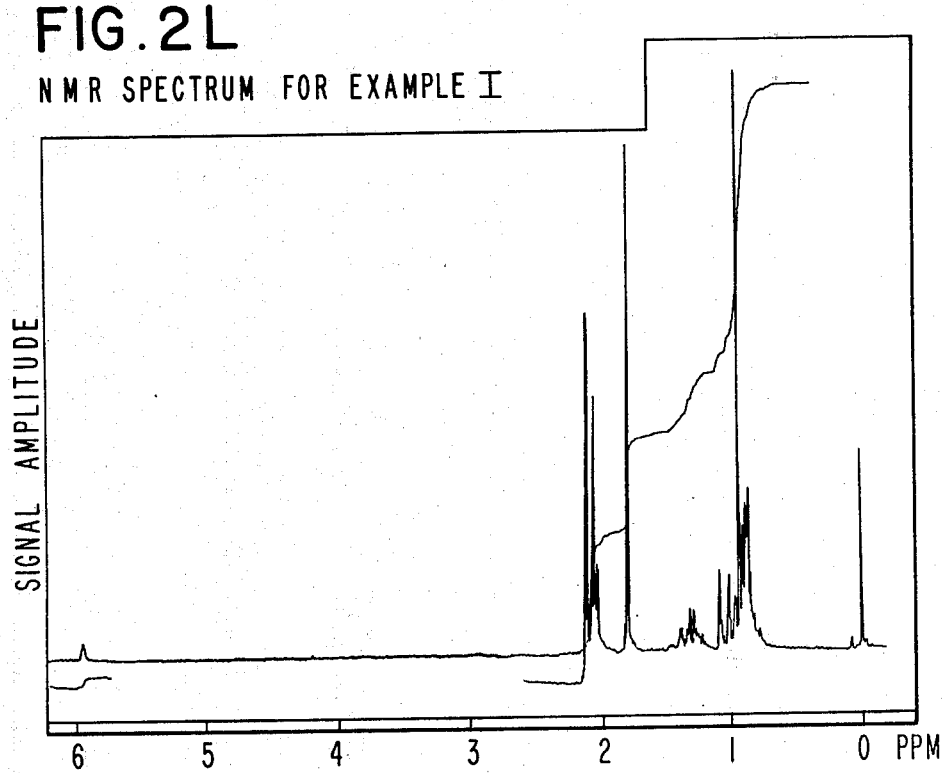

FIG. 2L represents the NMR spectrum for the compound containing the structure:

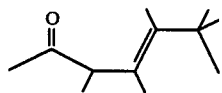

produced according to Example I.

FIG. 3 represents the GLC profile for the reaction product of Example II, containing a mixture of compounds, each of which is defined according to the generic structure:

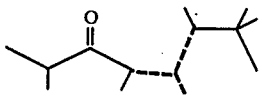

wherein in each of the molecules, one of the dashed lines represents a carbon-carbon double bond and each of the other of the dashed lines represent a carbon-carbon single bond.

FIG. 4 represents the infra-red spectrum for the reaction product of Example II containing the compounds having the structures:

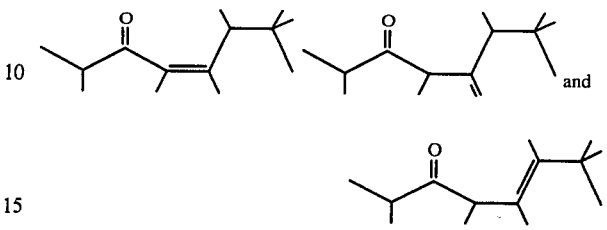

FIG. 5 represents the mass spectrum for the reaction product of Example II containing the compounds having the structures:

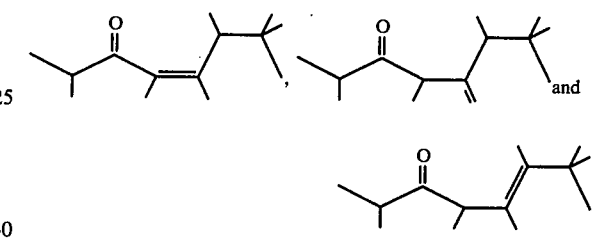

FIG. 6 represents the GLC profile for the reaction product of Example IIIA containing structures defined according to the genus having the structure:

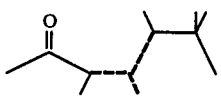

wherein in each of the molecules of the mixture, one of the dashed lines represents a carbon-carbon double bond and each of the other of the dashed lines represent carbon-carbon single bonds.

Figure 7:
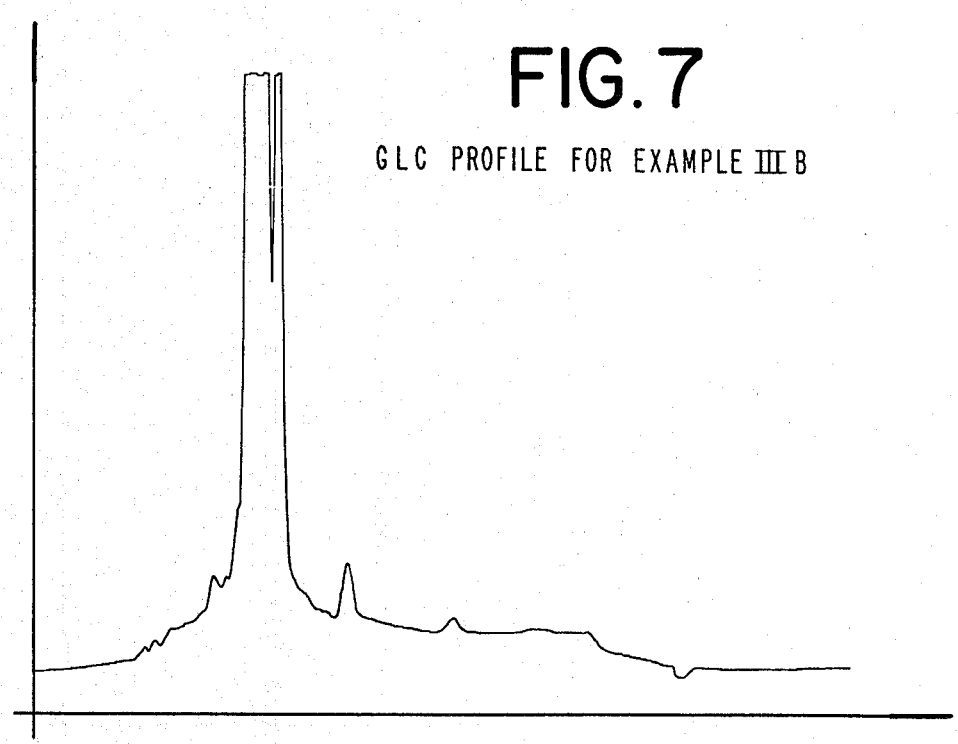

FIG. 7 represents the GLC profile for the reaction product of Example IIIB containing a mixture of compounds defined according to the structure:

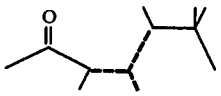

wherein in each of the molecules of the mixture, one of the dashed lines represents a carbon-carbon double bond and each of the other of the dashed lines represent carbon-carbon single bonds.

Figure 8:
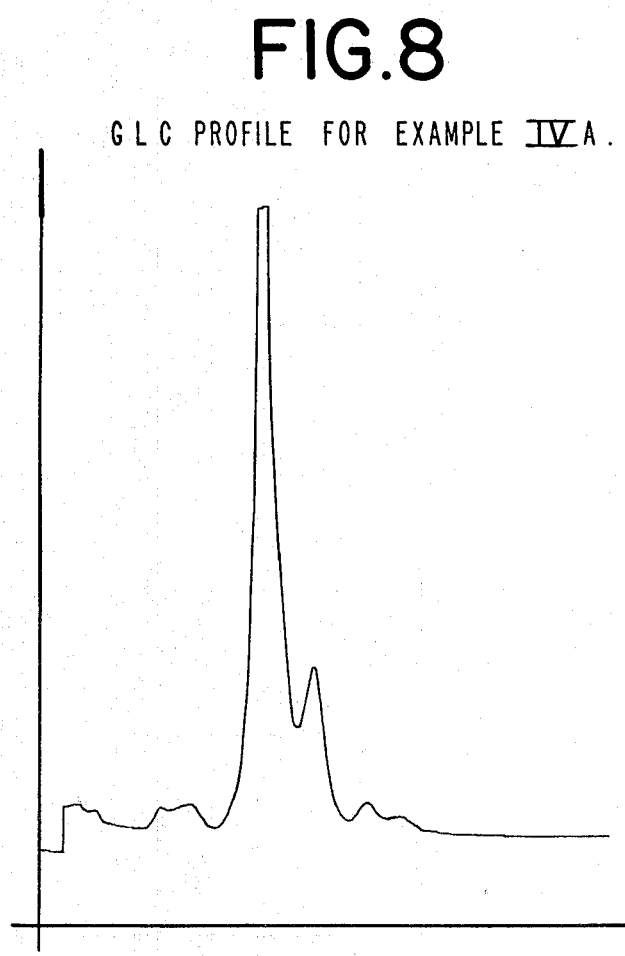

FIG. 8 represents the GLC profile for the reaction product of Example IVA containing a mixture of compounds defined according to the genus having the structure:

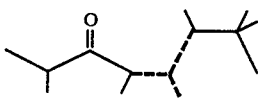

wherein in each of the molecules of the mixture, one of the dashed lines represents a carbon-carbon double bond and each of the other of the dashed lines represents carbon-carbon single bonds.

Figure 9:
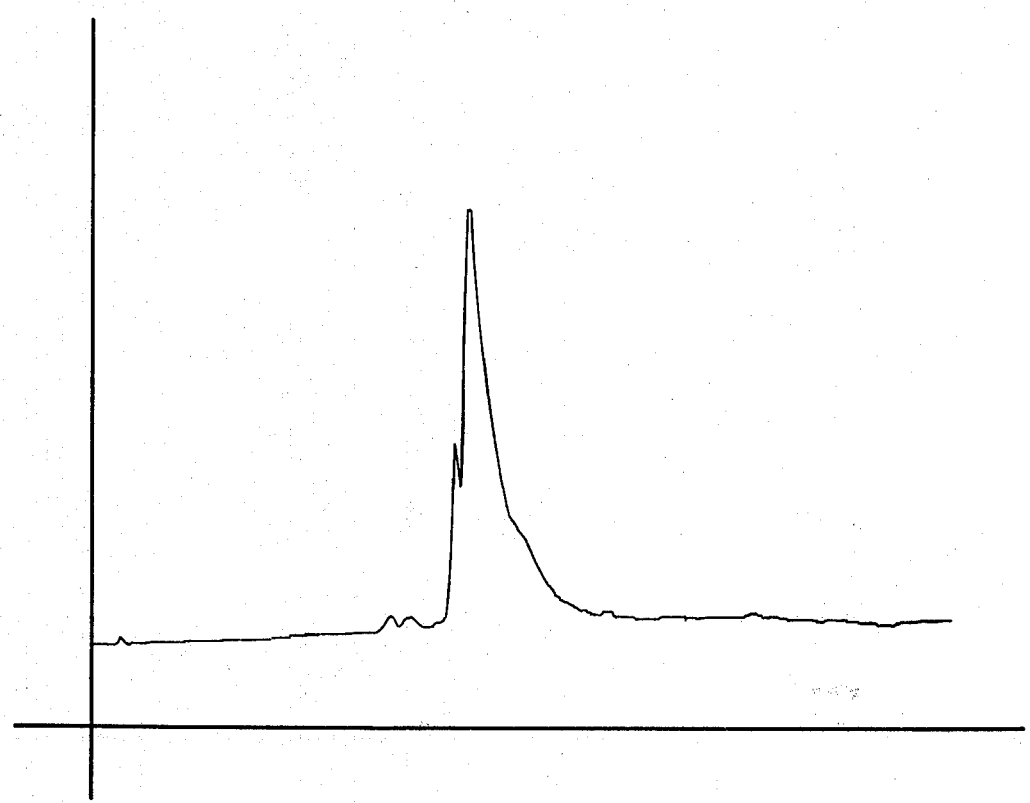

FIG. 9 is the GLC profile for the reaction product mixture prepared according to Example V (conditions: S.F. 96 column, 6 foot×¼ inch; programmed at 100°–220° C. at 8° C. per minute).

FIG. 10 is the infra red spectrum for the reaction product mixture prepared according to Example V containing compounds defined according to the structure:

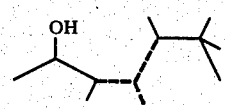

FIG. 11 is the GLC profile for fraction 4 of the distillation product of the reaction product of Example VI containing the compounds defined according to the structure:

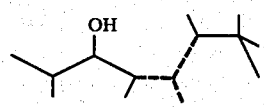

FIG. 12 is the infra red spectrum for the reaction product of Example VI containing the compounds having the structure:

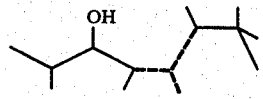

wherein in each of the compounds one of the dashed lines represents a carbon-carbon double bond and each of the other of the compounds represent carbon-carbon single bonds.

FIG. 13 is the NMR spectrum for fraction 4 of the distillation product of the reaction product of Example IV containing the compounds defined according to the structure:

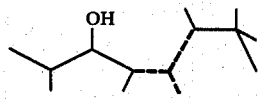

wherein in each of the compounds of the mixture one of the dashed lines represents a carbon-carbon double bond and each of the other of the compounds represent carbon-carbon single bonds.

DISCLOSURES INCORPORATED BY REFERENCE HEREIN

The following applications for U.S. Letters Patent are incorporated by reference herein:

(a) U.S. application for Letters Patent Ser. No. 160,788 filed on June 19, 1980 Pat. No. 4,287,084 (entitled: "Use of Mixture of Aliphatic $C_{10}$ Branched Olefins in Augumenting or Enhancing the Aroma of Perfumes and/or Perfumed Articles") setting forth the use of the compounds having the structures:

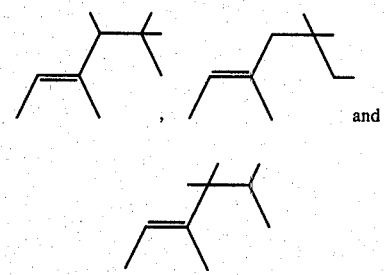

or generically the compounds defined according to the structure:

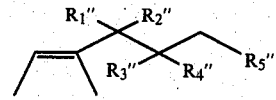

wherein $R_1''$, $R_2''$, $R_3''$, $R_4''$ and $R_5''$ represents hydrogen or methyl with three of $R_1''$, $R_2''$, $R_3''$, $R_4''$ and $R_5''$ representing methyl and the other two of $R_1''$, $R_2''$, $R_3''$, $R_4''$, and $R_5''$, representing hydrogen;

(b) U.S. Pat. No. 4,303,555 a continuation-in-part of Pat. No. 4,287,084; and (c) U.S. Pat. No. 4,321,255 entitled "Branched Ketones, Organoleptic Uses Thereof and Process for Preparing Same" disclosing the reaction:

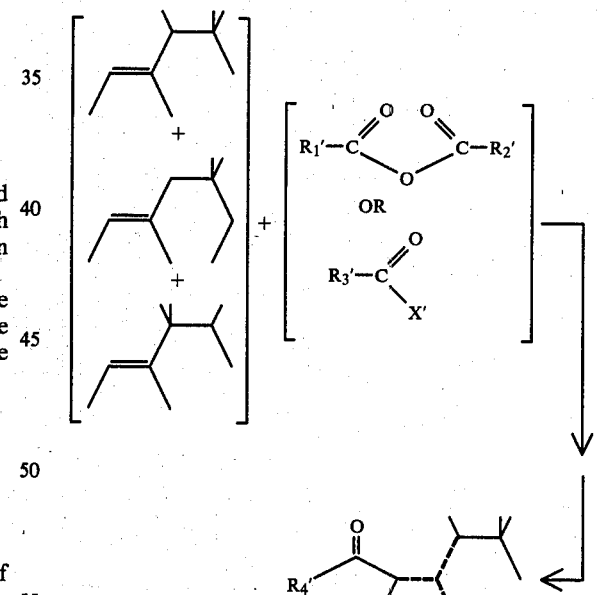

wherein $R_1'$, $R_2'$ and $R_3'$ represent $C_1$–$C_3$ lower alkyl and $R_4'$ is either of $R_1'$, $R_2'$ or $R_3'$ and wherein $X'$ is chloro or bromo, and the use of the resulting compounds for their organoleptic properties.

The instant application is directed to the use of the compounds defined according to the generic structure:

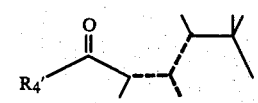

as starting materials wherein $R_4'$ is $C_1$–$C_3$ lower alkyl and wherein one of the dashed lines represents a carbon-carbon double bond and each of the other of the dashed lines represent carbon-carbon single bonds produced according to the process of U.S. Pat. No. 4,321,255 entitled "Branched Ketones, Organoleptic Uses Thereof and Process for Preparing Same."

THE INVENTION

It has now been determined that certain branched chain olefinic secondary alcohols are capable of imparting a variety of flavors and fragrances to various consumable materials. Briefly, our invention contemplates branched chain unsaturated secondary alcohols defined according to the generic structure:

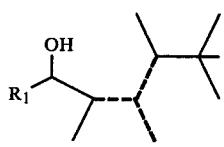

wherein $R_1$ represents methyl or isopropyl alcohol and wherein the dashed lines represents a carbon-carbon double bond and each of the other of the dashed lines represent carbon-carbon single bonds.

The branched chain olefinic secondary alcohols of our invention are either usable in admixture with one another, or the isomers are usable in admixture with one another such as mixtures of compounds defined according to the structure:

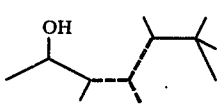

wherein one of the dashed lines in each of the molecules of the mixture represents a carbon-carbon double bond and each of the other of the dashed lines of each of the molecules of the mixture represent carbon-carbon single bonds or they may be used as individual compounds which are, for example, defined according to structures such as:

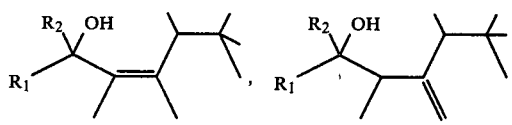

(wherein $R_1$ is methyl or isopropyl and $R_2$ is hydrogen)

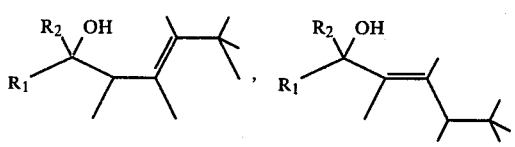

and 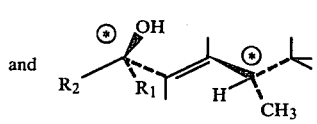

wherein the compound having the structure:

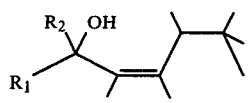

differs from the compound having the structure:

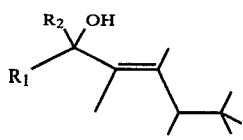

and that one is "cis" with respect to the methyl groups on the carbon atoms which make up the carbon-carbon double bond and wherein the structure:

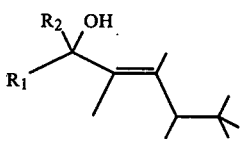

represents a "trans" isomer with respect to the methyl moieties bonded to the carbon atoms making up the carbon-carbon double bond and wherein the structure:

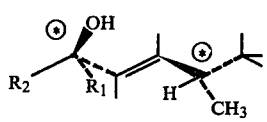

represents a stereo isomeric configuration wherein the carbon atoms having the "*" are asymetric carbon atoms in the molecule and wherein the compound is a "trans" isomer with respect to the methyl moieties bonded to the carbon atoms which make up the carbon-carbon double bond.

The branched chain olefinic secondary alcohols of our invention are obtained by means of reaction of the ketones produced according to U.S. Pat. No. 4,321,255 entitled "BRANCHED KETONES, ORGANOLEPTIC USES THEREOF AND PROCESS FOR PREPARING SAME" with a reducing agent such as:

(a) one or more alkali metal borohydrides, e.g. sodium borohydride, lithium borohydride and potassium borohydride;

(b) hydrogen, using a catalyst such as 5% palladium on carbon, 5% palladium on calcium carbonate or palladium on barium sulfate (e.g. "Lindlar Catalyst"); or (c) lithium aluminum hydride;

(d) aluminum alkoxides, such as aluminum isopropyxide and aluminum secondary epoxide, according to the reaction:

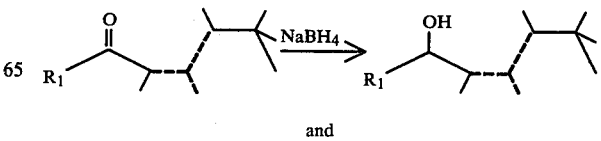

and

-continued

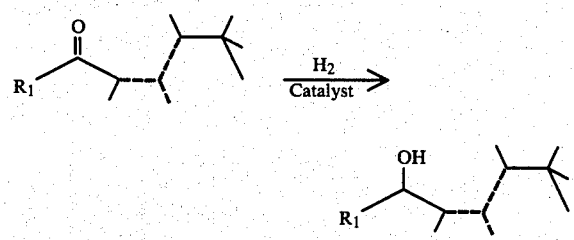

or, in general,

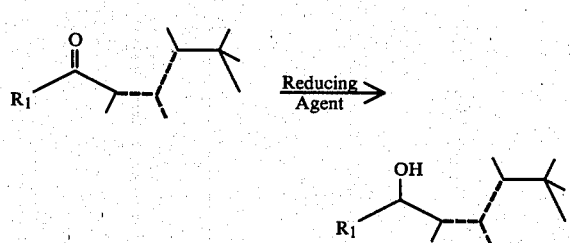

When carrying out the reaction for reacting the ketone having the structure:

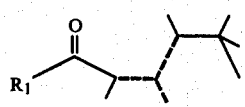

with an alkali metal borohydride such as sodium borohydride the reaction is carried out in the presence of a protic solvent which reacts relatively slowly or not at all with the alkali metal borohydride when compared to the reaction of the alkali metal borohydride with the ketone having the structure:

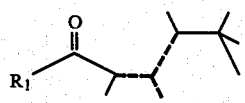

Specific workable solvents which must "solvate" the carbonyl moiety in order to enable the reaction to proceed at a reasonable rate are isopopyl alcohol, n-propenol, n-butanol, isobutyl alcohol and p-butyl alcohol.

The temperature of reaction is necessarily a function of:
 (i) the yield desired
 (ii) the time of reaction
 (iii) the nature of the solvent used
 (iv) the pressure of the vapor over the reaction mass
 (v) the concentration of the reactant, the alkali metal borohydride and the ketone having the structure:

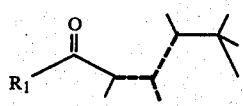

in the solvent
 (vi) the desired rate of reaction, and
 (vii) the ratio of alkali metal borohydride:ketone having the structure:

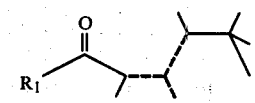

It is preferred to carry out the reaction at reflux conditions at atmospheric pressure. Thus, when using isopopyl alcohol as a solvent where the mole ratio fo alkali metal, borohydride:ketone having the structure:

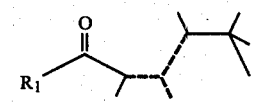

is 1:2, the temperature of reaction is about 73° C. and the time of reaction is 3 hours. In the case of using an alkali metal borohydride, the alcohol acts as a "solvent" and not as a "reactant".

On the other hand, when using the aluminum alkoxide such as aluminum secondary butoxide and aluminum isopropaxide, the solvent must be a source of hydrogen which is the actual reducing agent in the reaction. Thus, it is necessary that the "solvent" be a "reactable solvent" such as isopropyl alcohol and not merely a solvating solvent.

The mole ratio of alkali metal borohydride:ketone having the structure:

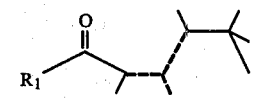

is preferably 1:2, which means that the equivalent ratio regarding hydrogen:ketone is 2:1; that is, the alkali metal borohydride is in 100% excess since theoretically only one mole of the alkali metal borohydride is needed to react with 4 moles of ketone, since one mole of alkali metal borohydride provides 4 atoms of hydrogen. Interestingly and surprisingly in this reaction and in all of the above reactions the double bond does get reduced during the reaction.

Insofar as the hydrogenation reaction is concerned with the ketone having the structure:

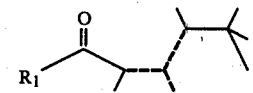

as the starting material or one of the ketones defined according to the structure:

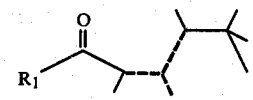

as being a starting material, the ketone is reacted with hydrogen in the presence of a Raney nickel catalyst or a palladium on carbon catalyst or a "Lindlar" catalyst (palladium on calcium carbonate) or palladium on barium sulfate. The percentage of palladium in the palladium on carbon catalyst or in the palladium on calcium carbonate catalyst or in the palladium on barium sulfate catalyst varies from about 2% up to about 7% with a percentage of palladium in the palladium on carbon catalyst or in the palladium on calcium carbonate catalyst or in the palladium on barium sulfate catalyst being preferred to be 5%. The temperature of reaction for the hydrogenation may vary from about 10° C. up to about 100° C. with a preferred reaction temperature of 25° C.-35° C. Since the reaction is exothermic it is usually necessary to provide external cooling to the reaction mass during the course of the reaction. The pressure of hydrogen over the reaction mass may vary from about 5 psig up to about 100 psig with the most preferred pressure being 20 psig. Pressures greater than 150 psig will give rise to amounts of fully saturated alcohol. The hydrogenation reaction may be carried out in the presence of or in the absence of a solvent. When a solvent is used, it is required that it be an inert (non-reactive) solvent such as isopropyl alcohol, hexane or ethanol. If a solvent is used it is preferred that the mole ratio of solvent:ketone having the structure:

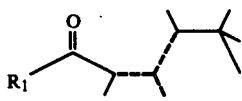

be approximately 1:1. Whereas a palladium containing catalyst is used the percentage of catalyst in the reaction mass may vary from 0.125% up to about 2.0% with a percentage of catalyst of about 0.25% being preferred. Where a Raney nickel catalyst is used, the percentage of catalyst in the reaction mass may vary from about 3% up to about 10% with a percentage of catalyst of about 5% being preferred.

If the reaction is carried out in the presence of the alkali metal borohydride, the reaction mass is neutralized using weak acid and the reaction product is then further washed with water and if necessary sodium carbonate. In any event, the reaction mass is ultimately distilled fractionally to yield the desired saturated alcohol product having the generic structure:

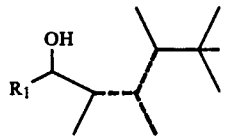

wherein $R_1$ is methyl or isopropyl and one of the dashed lines represents carbon-carbon double bond and the other of the dashed lines represents carbon-carbon single bonds.

Examples of branched chain unsaturated alcohols of my invention and their perfumery and tobacco flavor properties according to my invention are as follows:

TABLE I

| Identification of Secondary Alcohol | Organoleptic Properties | |
|---|---|---|
| | Perfumery Properties | Tobacco Properties |
| Mixture of compounds defined according to the structure:<br>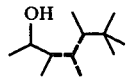 | A woody, amber, fruity aroma with strong vetiver nuances on dry-out after six hours | An intense woody, oriental-like and minty aroma and taste both prior to and on smoking in the mainstream and the sidestream |
| wherein in each component of the mixture one of the dashed lines represents a carbon-carbon double bond and each of the other of the dashed lines represents carbon-carbon single bond, produced according to the process of Example V, infra. Mixture of compounds defined according to the structure:<br>OH | An intense woody aroma | An oriental woody aroma and taste both prior to and on smoking in the mainstream and in the sidestream |
| wherein in each of the molecules of the mixture one of the dashed lines represents a carbon-carbon double bond and each of the other of the dashed lines represents carbon-carbon single bonds, prepared according to the process of Example VI, distillation fraction 4, infra. | | |

The individual branched chain secondary alcohols of our invention can be obtained in purer form or in substantially pure form by conventional purification techniques. Thus, the products can be purified by distillation, extraction, crystallization, preparative chromatographic techniques (including high pressure liquid chromatography) and the like. It has been found desirable to purify the branched chain unsaturated secondary alcohols of our invention by fractional distillation under vacuum.

It will be appreciated from the present disclosure that the branched chain secondary alcohols and mixtures thereof according to the present invention can be used to alter, vary, fortify, modify, enhance or otherwise improve the flavor and aroma of a wide variety of materials which are ingested, consumed or otherwise organoleptically sensed, particularly including perfume compositions, perfumed articles and smoking tobacco compositions and smoking tobacco articles.

The term "alter" in its various forms will be understood herein to mean the supplying or imparting of a flavor character or note or aroma character to an otherwise bland, relatively aromaless or tasteless substance, or augmenting an existing flavor or aroma characteristic where the natural flavor or aroma is deficient in some regard or supplementing the existing flavor or aroma impression to modify the organoleptic character.

The term "enhance" is intended herein to mean the intensification of a particular aroma or taste nuance (particularly in perfumes, perfumed articles or smoking tobaccos) without the changing of the quality of said nuance and without adding an additional aroma or taste nuance to the consumable material, the organoleptic properties of which are enhanced.

The term "tobacco" will be understood herein to mean a natural product such as, for example, burley, Turkish tobacco, Maryland tobacco, flue-cured tobacco and the like including tobacco-like or tobacco-based products such as reconstituted or homogenized leaf and the like, as well as tobacco substitutes intended to replace natural tobacco, such as lettuce and cabbage leaves and the like. The tobaccos and tobacco products in which the branched chain unsaturated secondary alcohols of my invention are useful include those designed or used for smoking such as in cigarette, cigar and pipe tobacco, as well as products such as snuff, chewing tobacco and the like.

The branched chain unsaturated secondary alcohols of my invention can be used to contribute warm, vetiver-like, woody, fruity and amber aromas. As olfactory agents the branched chain unsaturated secondary alcohols of this invention can be formulated into or used as components of a "perfume composition".

The term "perfume composition" is used herein to mean a mixture of organic compounds, including, for example, alcohols, other than the alcohols of this invention, aldehydes, ketones, nitriles, esters, and frequently hydrocarbons which are admixed so that the combined odors of the individual components produce a pleasant or desired fragrance. Such perfume compositions usually contain: (a) the main note of the "bouquet" or foundation-stone of the composition; (b) modifiers which round off and accompany the main note; (c) fixatives which include odorous substances which lend a particular note to the perfume throughout all stages of evaporation, and substances which retard evaporation; and (d) topnotes which are usually low-boiling fresh-smelling materials.

In perfume compositions, the individual component will contribute its particular olfactory characteristics but the overall effect of the perfume composition will be the sum of the effect of each ingredient. Thus, the individual compounds of this invention, or mixtures thereof, can be used to alter the aroma characteristics of a perfume composition, for example, by highlighting or moderating the olfactory reaction contributed by another ingredient in the composition.

The amount of branched chain unsaturated secondary alcohols of this invention which will be effective in perfume compositions depends on many factors, including the other ingredients, their amounts and the effects which are desired. It has been found that perfumed compositions containing as little as 0.05% and as much as 5% of the branched chain unsaturated secondary alcohols of this invention can be used to impart, augment or enhance warm, intense, amber, woody, fruity and vetiver aroma profiles to soaps, cosmetics, solid or liquid anionic, cationic, nonionic and zwitterionic detergents and other products. The amount employed can range up to 50% of the fragrance and can be as low as 1% of the original fragrance and will depend on considerations of cost, nature of the end product, the effect desired in the finished product and the particular fragrance sought.

The branched chain unsaturated secondary alcohols of this invention can be used alone or in a perfume composition as an olfactory component in detergents, and soaps, space odorants and deodorants, perfumes, colognes, toilet waters, bath salts, hair preparations such as lacquers, brilliantines, pomades, and shampoos, cosmetic preparations such as creams, deodorants, hand lotions and sun screens, powders such as talcs, dusting powders, face powder, and the like. When used as an olfactory component of a perfumed article, as little as 0.05% of one or more of the branched chain unsaturated secondary alcohols will suffice to impart warm, vetiver, woody, amber and fruity aroma nuances. Generally no more than 5.0% is required.

In addition, the perfume composition can contain a vehicle or carrier for the branched chain unsaturated secondary alcohols taken alone or taken together with other ingredients. The vehicle can be a liquid such as an alcohol such as ethanol, a glycol such as propylene glycol, or the like. The carrier can be an absorbent solid such as a gum or a microporous polymer or components for encapsulating the composition such as by means of coacervation.

An additional aspect of our invention provides an organoleptically improved smoking tobacco product and additives therefor, as well as methods of making the same which overcome specific problems heretofore encountered in which specific desired oriental and woody and minty flavor and aroma characteristics are created or enhanced and may be readily controlled and maintained at the desired uniform level regardless of variations in the tobacco components of the blend.

This invention further provides improved tobacco additives and methods whereby various desirable woody, oriental and minty flavor and aroma characteristics may be imparted to smoking tobacco products and may be readily varied and controlled to produce the desired uniform flavoring characteristics prior to and on smoking in the mainstream and in the sidestream.

In carrying out this aspect of our invention, we add to smoking tobacco materials or a suitable substitute therefor (e.g. dried lettuce leaves) an aroma and flavor additive containing as an active ingredient at least one of the secondary alcohols of my invention.

In addition to the one or more secondary alcohols of my invention, other flavoring and aroma additives may be added to the smoking tobacco material or substitute therefor either separately or in admixture with the secondary alcohols as follows:

I. Synthetic Materials:
  Beta-ethyl-cinnamaldehyde;
  Eugenol;
  Dipentene;
  -Damascone;
  1-[3-(methylthio)butyrol]2,3,3-trimethyl-cyclohexene;
  -Damascenone;
  Maltol;
  Ethyl maltol;
  Delta undecalactone;
  Delta decalactone;
  Benzaldehyde;
  Amyl acetate;
  Ethyl butyrate;
  Ethyl acetate;
  2-Hexenol-1,2methyl-isopropyl-1,3-nonadiene-8-one;
  2,6-Dimethyl-2,6-undecadiene-10-one;
  2-Methyl-5-isopropyl acetophenone;
  2-Hydroxy-2,5,5,8a-tetramethyl-1-(2-hydroxyethyl)-decahydronaphthalene;
  Dodecahydro-3a,6,6,9a-tetramethyl naphtho-(2-1-b)furan;
  4-Hydorxy hexanoic acid, gamma lactone;
  Polyisoprenoid hydrocarbons defined in Example V of U.S. Pat. No. 3,589,372, issued on June 29, 1971.
II. Natural Oils
  Celery seed oil;
  Coffee extract;

Bergamot Oil;
Cocoa extract;
Nutmeg oil; and
Origanum oil.

An aroma and flavoring concentrate containing one or more of the secondary alcohols of my invention and if desired one or more of the above indicated additional flavoring additives may be added to the smoking tobacco material, to the filter or to the leaf or paper wrapper. The smoking tobacco material may be shredded, cured, cased and blended tobacco material or reconstituted tobacco material or tobacco substitutes (e.g., lettuce leaves) or mixtures thereof. The proportions of flavoring additives may be varied in accordance with taste but insofar as the augmentation, or the enhancement or the imparting of the woody, oriental and minty notes are concerned, we have found that satisfactory results are obtained if the proportion by weight of the sum total of secondary alcohols of my invention is between 250 ppm and 1,500 ppm (0.025%–1.5%) of the active ingredients to the smoking tobacco material. I have further found that satisfactory results are obtained if the proportion by weight of the sum total of secondary alcohols used to flavoring material is between 2,500 and 10,000 ppm (0.25%–1.5%).

Any convenient method for incorporating the secondary alcohols in the tobacco product may be employed. Thus, the secondary alcohols taken alone or along with other flavoring additives may be dissolved in a suitable solvent such as ethanol, n-pentane, diethyl ether and/or other volatile organic solvents and the resulting solution may either be sprayed on the cured, cased and blended tobacco material or the tobacco material may be dipped into such solution. Under certain circumstances, a solution of one or more secondary alcohols of this invention taken alone or further together with other flavoring additives as set forth above may be applied by means of a suitable applicator such as a brush or roller on the paper or leaf wrapper for the smoking product, or it may be applied to the filter by either spraying or dipping or coating.

Furthermore, it will be apparent that only a portion of the tobacco or substitute therefor need be treated and the thus treated tobacco may be blended with other tobaccos before the ultimate tobacco product is formed. In such cases, the tobacco treated may have one or more of the secondary alcohols of this invention in excess of the amounts of concentrations above indicated so that when blended with other tobaccos, the final product will have the percentage within the indicated range.

In accordance with one specific example of my invention, an aged, cured and shredded domestic burley tobacco is spread with a 20% ethyl solution of a mixture of compounds having the structure.

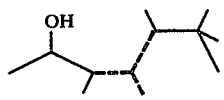

produced according to Example V, infra, in an amount to provide a tobacco composition containing 800 ppm by weight of the secondary alcohol mixture on a dry basis. Thereafter, the ethyl alcohol is removed by evaporation and the tobacco is manufactured into cigarettes by the usual techniques. The cigarette when treated as indicated has a desired and pleasing aroma which is detectable in the main and side streams when the cigarette is smoked. This aroma is described as being sweet, oriental-like, woody and turkish tobacco-like with intense minty nuances.

While our invention is particularly useful in the manufacture of smoking tobacco, such as cigarette tobacco, cigar tobacco and pipe tobacco, other tobacco products formed from sheeted tobacco dust or fines may also be used. Likewise, the secondary alcohols of my invention can be incorporated with materials such as filter tip materials, seam paste, packaging materials and the like which are used along with tobacco to form a product adapted for smoking. Furthermore, the secondary alcohols of this invention can be added to certain tobacco substitutes of natural or synthetic origin (e.g. dried lettuce leaves) and, accordingly, by term "tobacco" as used throughout this specification is meant any composition intended for human consumption by smoking or otherwise, whether composed of tobacco plant parts or substitute materials or both.

The following examples A–IV are given to illustrate techniques for producing the precursors for the compounds of my invention as it is presently preferred to practice it. Example V and onwards are given to illustrate embodiments of my invention as it is presently preferred to practice it. It will be understood that these examples are illustrative and the invention is to be considered restricted thereto except as indicated in the appended claims.

EXAMPLE A

PREPARATION OF DI-ISOAMYLENE DERIVATIVES

Reaction:

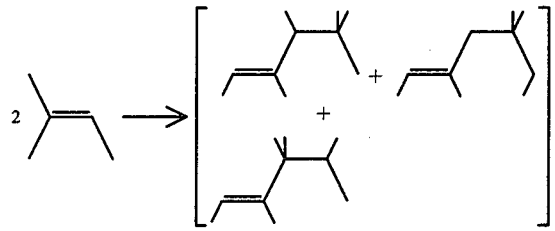

(wherein in each of the molecules indicated, one of the dashed lines is a carbon-carbon double bond and the other of the dashed lines are carbon-carbon single bonds).

Di-isoamylene is prepared according to one of the procedures set forth in the following references.

i - Murphy & Lane, Ind. Eng. Chem., Prod. Res. Dev., Vol. 14, No. 3, 1975 p. 167 (Title: Oligomerization of 2-Methyl-2-Butene in Sulfuric and Sulfuric-Phosphoric Acid Mixtures).

ii - Whitmore & Mosher, Vol. 68, J. Am. Chem. Soc., February, 1946, p. 281 (Title: The Depolymerization of 3,4,5,5-Tetramethyl-2-hexene and 3,5,5-Trimethyl-2-heptene in Relation to the Dimerization of Isoamylenes).

The resulting material was distilled in a fractionation column in order to separate the di-isoamylene from the higher molecular weight polymers, which are formed during the reaction as by-products.

FIG. AA represents the GLC profile for the reaction product of Example A using a 70% sulfuric acid catalyst at 35% C.

FIG. AB represents the GLC profile for the reaction product of Example A using an Amberlyst® 15 acidic ion exchange resin catalyst at a temperature of 150° C.

FIG. AC represents the GLC profile for the reaction product of Example A, using an Amberlyst® 15 catalyst at 100° C.

FIG. AD represents the GLC profile for the reaction product of Example A, using a sulfuric acid catalyst and an alpha-methylstyrene diluent at 35° C. according to the conditions of United Kingdom Patent Specification 796,130 (crude reaction product).

FIG. AE represents the GLC profile for the reaction product of Example I, using a sulfuric acid catalyst, at 35° C. and an alpha-methyl styrene diluent according to the conditions of United Kingdom Patent Specification 796,130 (distilled reaction product.

FIG. BA represents the NMR spectrum for Peak 1 of the GLC profile of FIG. AE.

FIG. BB represents the infra-red spectrum for Peak 1 of the GLC profile of FIG. AE.

FIG. CA represents the NMR spectrum for Peak 2 of the GLC profile of FIG. AE.

FIG. CB represents the infra-red spectrum for Peak 2 of the GLC profile of FIG. AE.

FIG. D represents the NMR spectrum for Peak 2 of the GLC profile of FIG. AB.

EXAMPLE I

PREPARATION OF ACETYL DERIVATIVE OF DIISOAMYLENE

Reaction:

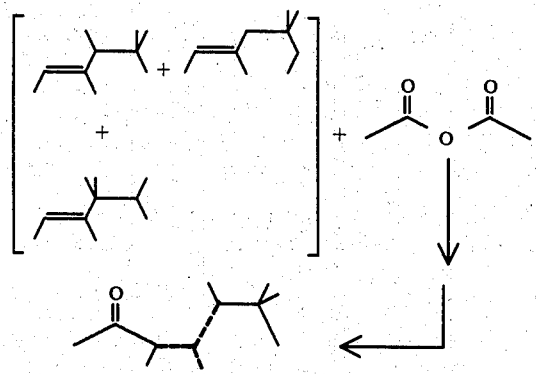

wherein in each of the structures containing dashed lines, these structures represent mixtures of molecules wherein in each of the molecules, one of the dashed lines represents a carbon-carbon double bond and each of the other of the dashed lines represent carbon-carbon single bonds.

Into a 2-liter reaction flask equipped with stirrer, thermometer, reflex condenser and heating mantle, is placed 1000 g of acetic anhydride and 80 g of boron trifluoride diethyl etherate. The resulting mixture is heated to 80° C. and, over a period of 40 minutes, 690 g of diisoamylene prepared according to the illustration in Example A, supra is added. The reaction mass is maintained at 82°–85° C. for a period of 5.5 hours, whereupon it is cooled to room temperature. The reaction mass is then added to one liter of water and the resulting mixture is stirred thereby yielding two phases; an organic phase and an aqueous phase. The organic phase is separated from the aqueous phase and neutralized with two liters of 12.5% sodium hydroxide followed by one liter of saturated sodium chloride solution. The resulting organic phase is then dried over anhydrous sodium sulfate and distilled in a one plate distillation column, yielding the following fractions:

| Fraction No. | Vapor Temp. (°C.) | Liquid Temp. (°C.) | mm/Hg Pressure | Weight of Fraction (g.) |
|---|---|---|---|---|
| 1 | 33/68 | 62/77 | 8/8 | 161 |
| 2 | 69 | 79 | 4 | 100 |
| 3 | 72 | 86 | 3.0 | 191 |
| 4 | 88 | 134 | 3.0 | 189 |

The resulting material is then distilled on a multi-plate fractionation column, yielding the following fractions at the following reflux ratios:

| Fraction No. | Vapor Temp. (°C.) | Liquid Temp. (°C.) | mm/Hg Pressure | Reflux Ratio R/D | Weight of Fraction (g.) |
|---|---|---|---|---|---|
| 1 | 30/65 | 62/83 | 5/5 | 9:1 | 30.8 |
| 2 | 68 | 84 | 5 | 9:1 | 52.8 |
| 3 | 68 | 85 | 5 | 9:1 | 34 |
| 4 | 69 | 87 | 5 | 9:1 | 43 |
| 5 | 69 | 87 | 5 | 9:1 | 34 |
| 6 | 71 | 88 | 4 | 4:1 | 41 |
| 7 | 70 | 88 | 5 | 4:1 | 36.5 |
| 8 | 71 | 91 | 5 | 4:1 | 42 |
| 9 | 73 | 95 | 3 | 4:1 | 42.5 |
| 10 | 80 | 106 | 3 | 4:1 | 39 |
| 11 | 80 | 142 | 3 | 4:1 | 50.8 |
| 12 | 80 | 220 | 3 | 4:1 | 24 |

GLC, NMR, IR and mass spectral analyses yield the information that the resulting material is a mixture of cis and trans isomers having a generic structure:

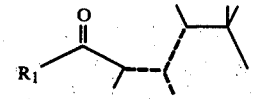

wherein in each of the molecules, one of the dashed lines is a carbon-carbon double bond and the other of the dashed lines is a carbon-carbon single bond and, primarily, this mixture contains the molecular species (cis and trans isomers) as follows:

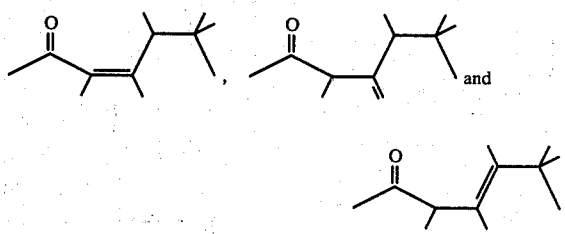

FIG. 1 sets forth the GLC profile for the reaction product of Example I, containing compounds defined according to the structure:

wherein in each molecule of the mixture, one of the dashed lines is a carbon-carbon double bond and the other of the dashed lines are carbon-carbon single bonds.

FIG. 2A represents the infra-red spectrum of Peak 3 of the GLC profile of FIG. 1.

FIG. 2B represents the infra-red spectrum of Peak 4 of the GLC profile of FIG. 1.

FIG. 2C represents the infra-red spectrum for Peak 5 of the GLC profile of FIG. 1.

FIG. 2D represents the infra-red spectrum for Peak 7 of the GLC profile of FIG. 1.

FIG. 2E represents the infra-red spectrum for Peak 7 of the GLC profile of FIG. 1.

FIG. 2F represents the infra-red spectrum for Peak 8 of the GLC profile of FIG. 1.

FIG. 2G represents the infra-red spectrum for Peak 9 of the GLC profile of FIG. 1.

FIG. 2K represents the NMR spectrum for the compound having the structure:

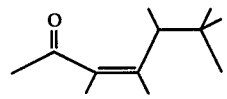

produced according to Example I.

FIG. 2L represents the NMR spectrum for the compound containing the structure:

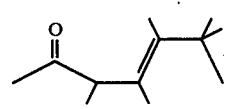

produced according to Example I.

EXAMPLE II

PREPARATION OF ISOBUTYRYL DERIVATIVE OF DIISOAMYLENE

Reaction:

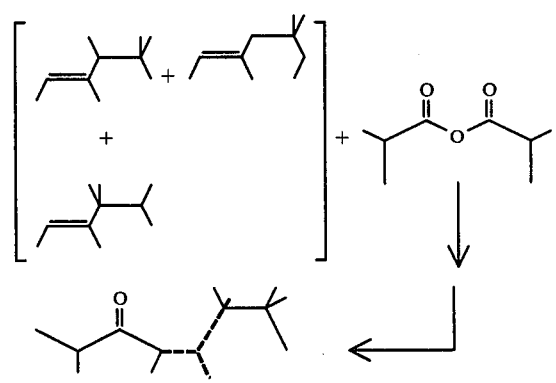

wherein in each of the structures containing dashed lines, these structures represent mixtures of molecules wherein in each of the molecules, one of the dashed lines represents a carbon-carbon double bond and each of the other of the dashed lines represent carbon-carbon single bonds.

Into a 5-liter reaction flask, equipped with reflux condenser, addition funnel, thermometer, Thermowatch, heating mantle and nitrogen purge accessory is placed 1361 g (8.6 moles) of isobutyric anhydride. 105 ml (0.86 moles) of boron trifluoride etherate is then added to the isobutyric anhydride. The resulting mixture is then heated to 65° C. Over a period of 4 hours, 1725 g (8.6 moles) of diisoamylene prepared according to the illustration of Example A is added to the reaction mass, while maintaining the reaction mass at a temperature of 83°–85° C.

The reaction mass is then cooled to room temperature and is added to a 5-liter separatory funnel. 75 ml of 50% sodium hydroxide (aqueous) and 100 ml water is then added to the reaction mass thus yielding two phases, an aqueous phase and an organic phase. The lower aqueous phase is removed and the organic phase is washed as follows:

A - 1 liter saturated sodium chloride
B - 1 liter 5% aqueous sodium hydroxide
C - 1 liter saturated sodium chloride
D - 1 liter 12.5% sodium hydroxide
E - 1 liter 12.5% sodium hydroxide The reaction mass is then distilled on a two inch splash column packed with stones yielding the following fractions:

| Fraction No. | Vapor Temp. (°C.) | Liquid Temp. (°C.) | mm/Hg Pressure | Weight of Fraction (g.) |
|---|---|---|---|---|
| 1 | 29/54 | 54/68 | 29/24 | Starting Material |
| 2 | 51 | 68 | 14 | " |
| 3 | 90 | 68 | 11 | " |
| 4 | 64 | 98 | 11 | " |
| 5 | 92/94 | 102/108 | 7/5 | 378 |
| 6 | 135 | 165 | 5 | 257 |

Fractions 5 and 6 of the resulting distillate are then bulked and redistilled yielding the following fractions:

| Fraction No. | Vapor Temp. (°C.) | Liquid Temp. (°C.) | mm/Hg Pressure | Reflux Ratio R/D | Weight of Fraction (g.) |
|---|---|---|---|---|---|
| 1 | 15/45 | 88/92 | 3/2.5 | 4:1 | 21 |
| 2 | 60 | 99 | 2.4 | 4:1 | 13 |
| 3 | 67 | 98 | 2.4 | 4:1 | 35 |
| 4 | 69 | 97 | 2.2 | 4:1 | 49 |
| 5 | 70 | 99 | 2.2 | 4:1 | 59 |
| 6 | 70 | 101 | 2.2 | 4:1 | 50 |
| 7 | 70 | 101 | 2.0 | 4:1 | 37 |
| 8 | 84 | 112 | 1.7 | 4:1 | 33 |
| 9 | 84 | 112 | 1.7 | 4:1 | 63 |
| 10 | 78 | 119 | 1.8 | 4:1 | 37 |
| 11 | 84 | 122 | 1.7 | 4:1 | 51 |
| 12 | 92 | 121 | 1.7 | 4:1 | 43 |
| 13 | 101 | 156 | 1.6 | 4:1 | 27 |
| 14 | 121 | 178 | 1.6 | 4:1 | 85 |
| 15 | 110 | 220 | 1.6 | 4:1 | 33 |

Fractions 3–9 of this distillation are then rebulked and redistilled on a 12 inch Goodloe Silver Mirror column yielding the following fractions:

| Fraction No. | Vapor Temp. (°C.) | Liquid Temp. (°C.) | mm/Hg Pressure | Reflux Ratio R/D | Weight of Fraction (g.) |
|---|---|---|---|---|---|
| 1 | 47/60 | 84/92 | 1.6/1.2 | 4:1 | |
| 2 | 67 | 93 | 1.2 | 4:1 | 50 |
| 3 | 67 | 94 | 1.2 | 4:1 | 50 |
| 4 | 67 | 95 | 1.2 | 4:1 | 52 |
| 5 | 67 | 95 | 1.2 | 4:1 | 50 |
| 6 | 67 | 98 | 1.2 | 4:1 | 57 |
| 7 | 67 | 101 | 1.2 | 4:1 | 57 |
| 8 | 72 | 212 | 1.2 | 4:1 | 42 |

The resulting reaction product is analyzed by means of GLC, NMR, IR and mass spectral analyses and this confirms that the reaction product is a mixture of compounds defined according to the generic structure:

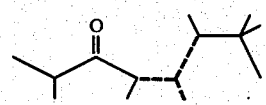

wherein in each of the molecules, one of the dashed lines is a carbon-carbon double bond and the other two of the dashed lines represent carbon-carbon single bonds. The major components of this mixture are compounds having the structures:

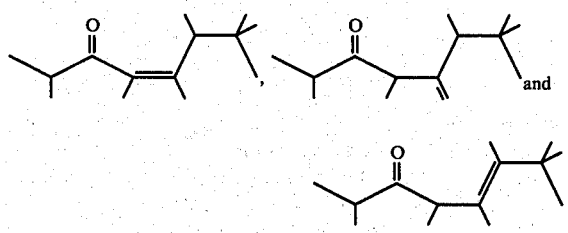

FIG. 3 represents the GLC profile for the reaction product of Example II, containing a mixture of compounds, each of which is defined according to the generic structure:

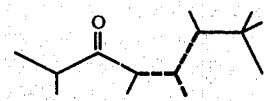

wherein in each of the molecules, one of the dashed lines represents a carbon-carbon double bond and each of the other of the dashed lines represent carbon-carbon single bonds.

FIG. 4 represents the infra-red spectrum for the reaction product of Example II containing the compounds having the structures:

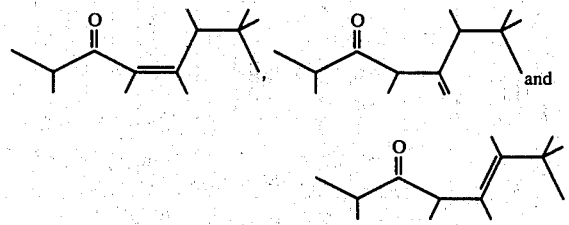

FIG. 5 represents the mass spectrum for the reaction product of Example II containing the compounds having the structures:

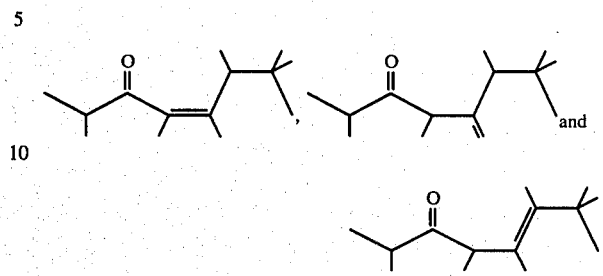

EXAMPLE III

PREPARATION OF ACETYL DERIVATIVE OF DIISOAMYLENE

Reaction:

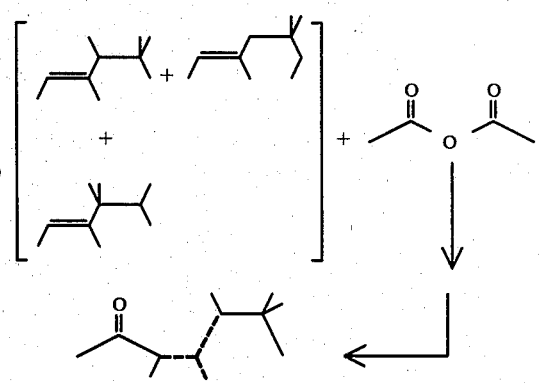

EXAMPLE IIIA

Into a 5-liter reaction flask equipped with electric stirrer, thermometer, addition funnel, 24/42 y-tube, condenser, heating mantle and nitrogen purge accessories are added 41 ml of 70% methane sulfonic acid followed by 30 g of phosphorous pentoxide. The resulting mixture exotherms to 60° C.

Over a period of 7 minutes, 235 ml acetic anhydride is added to the reaction mass while maintaining same at a temperature of 65° C. Over a period of 30 minutes while maintaining the reaction temperature at 80° C., 516 ml of diisoamylene prepared according to the illustration of Example A is added dropwise to the reaction mass. At the end of the addition of the diisoamylene, GLC analysis indicates 42% product.

The reaction mass is added to a 5 gallon open head separatory flask containing 1 liter of water.

The resulting mixture is washed with 1 liter of 12% sodium hydroxide followed by 1 liter of saturated sodium chloride solution. 100 ml toluene is added to help separation.

GLC, NMR, IR and mass spectral analyses yield the information that the resulting organic phase is a mixture of compounds defined according to the generic structure:

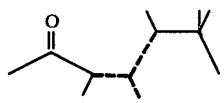

wherein in each of the molecules one of the dashed lines is a carbon-carbon double bond and the other two of the dashed lines represent carbon-carbon single bonds.

The resulting reaction product is then dried over anhydrous magnesium sulfate and distilled on a 3-inch stone column yielding the following fractions:

| Fraction No. | Vapor Temp. (°C.) | Liquid Temp. (°C.) | mm/Hg Pressure |
|---|---|---|---|
| 1 | 65/65 | 103/92 | 113/35 |
| 2 | 60 | 80 | 1 |
| 3 | 52 | 89 | 1 |
| 4 | 61 | 134 | 1 |
| 5 | 73 | 140 | 1 |

Fraction 2, 3 and 4 are bulked and evaluated for their organoleptic properties.

FIG. 6 represents the GLC profile for the reaction product of Example IIIA containing structures defined according to the genus having the structure:

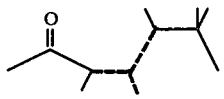

wherein in each of the molecules of the mixture, one of the dashed lines represents a carbon-carbon double bond and each of the other of the dashed lines represent carbon-carbon single bonds.

To a 500 ml reaction flask equipped with reflux condenser, addition funnel, thermometer, Thermowatch, heating mantle, cooling bath and nitrogen purge accessories, is added 406 ml of acetic anhydride and 30 ml boron trifluoride etherate. The reaction mass is heated to 60° C. and while maintaining the reaction mass at 60° over a period of 30 minutes, diisoamylene, prepared according to the illustration of Example A is added. The resulting reaction mass is then heated, with stirring at 60° C. for a period of 12 hours. At the end of the 12 hour period, the reaction mass is distilled yielding the following fractions:

| Fraction No. | Vapor Temp. (°C.) | Liquid Temp. (°C.) | mm/Hg pressure | Weight of Fraction (g.) |
|---|---|---|---|---|
| 1 | 50/58 | 60/70 | 2.5 | 330 |
| 2 | 67 | 87 | 1.4 | 329 |
| 3 | 71 | 88 | 3.0 | 65 |
| 4 | 90 | 115 | 3.0 | 195 |

The resulting mass, by GLC, IR, NMR and mass spectral analyses consist of compounds defined according to the generic structure:

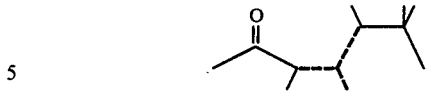

wherein in each of the molecules one of the dashed lines is a carbon-carbon double bond and the other two of the dashed lines represent carbon-carbon single bonds.

FIG. 7 sets forth the GLC profile for the reaction product of this Example IIIB.

EXAMPLE IV

PREPARATION OF ISOBUTYRO DERIVATIVE OF DIISOAMYLENE

Reaction:

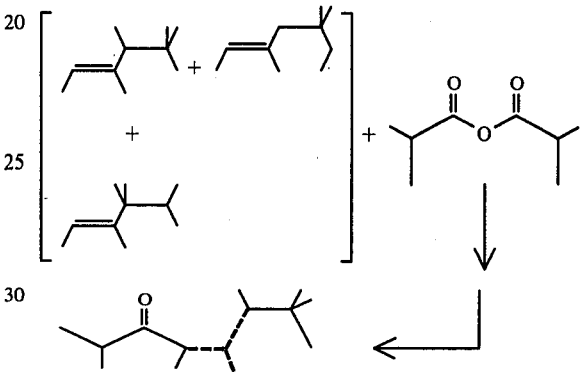

wherein in each of the structures containing dashed lines, these structures represent mixtures of molecules wherein in each of the molecules, one of the dashed lines represents a carbon-carbon double bond and each of the other of the dashed lines represent carbon-carbon single bonds.

Into a 5000 ml reaction flask equipped with reflux condenser, addition funnel, thermometer, Thermowatch, heating mantle, cooling bath and nitrogen gas purge accessory, is added 953 ml (6.0 moles) of isobutyric anhydride; 183 g of polyphosphoric acid and 135 ml 70% methane sulfonic acid. The reaction mass exotherms to 65° C.

Over a period of 20 minutes, while maintaining the reaction mass at 65° C. 1725 g (8.6 moles) of diisoamylene prepared according to the illustration of Example A is added to the reaction mass. The reaction mass is then heated to 85° C. and maintained at that temperature for a period of 10 hours. At the end of the 10 hour period, the reaction mass is cooled and 100 g of sodium acetate and 1 liter of water are added thereto. The resulting mixture is added to a 5 liter separatory funnel and the organic layer is then washed as follows:

A - 1 liter 12.5% sodium hydroxide
B - 2 liter 12.5% sodium hydroxide
C - 1 liter of saturated sodium chloride The reaction mass is then distilled on a 1 foot Goodloe column yielding the following fractions:

| Fraction No. | Vapor Temp. (°C.) | Liquid Temp. (°C.) | mm/hg Pressure | Reflux Ratio R/D | Weight of Fraction (g.) |
|---|---|---|---|---|---|
| 1 | 35/50 | 88/93 | 1.8/.08 | 4:1 | 41 |
| 2 | 63 | 100 | .8 | 4:1 | 48 |

| Fraction No. | Vapor Temp. (°C.) | Liquid Temp. (°C.) | mm/hg Pressure | Reflux Ratio R/D | Weight of Fraction (g.) |
|---|---|---|---|---|---|
| 3 | 63 | 105 | .6 | 4:1 | 73 |
| 4 | 66 | 114 | .6 | 4:1 | 44 |
| 5 | 100 | 145 | .6 | 4:1 | 42 |
| 6 | 101 | 225 | .6 | 4:1 | 29 |

GLC, NMR, IR and mass spectral analyses confirm the information that the resulting product is a mixture of compounds defined according to the generic structure:

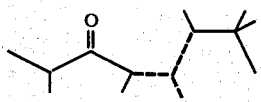

wherein in each molecule of the mixture, one of the dashed lines is a carbon-carbon double bond and the other two of the dashed lines represent carbon-carbon signal bonds.

FIG. 8 sets forth the GLC profile for the reaction product of this Example (Conditions: SF 96 column, six foot × ¼ inch; operated at 180° C. isothermal).

EXAMPLE V

PREPARATION OF DIISOAMYLENE METHYL CARBINOL

Reaction:

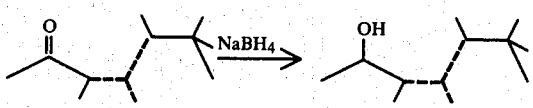

Into a 2 liter reaction flask equipped with reflux condenser, addition funnel, thermometer, heating mantle, and nitrogen bleed is placed 1 liter of isopropyl alcohol followed by 38 grams of sodium borohydride. The resulting mixture is heated to reflux and over a period of 40 minutes while maintaining the reflux temperature at 48° C. dropwise addition of acetyl diisoamylene prepared according to Example III (368 grams)(bulked fractions 2–12 of the distillation) is carried out.

At the end of the addition of the 368 grams of acetyl diisoamylene, the reaction mass is stirred at a temperature of 73° C. for a period of 3 hours. The reaction mass is then transferred to a separatory flask containing 1 liter of water. 200 ml 5% hydrochloric acid is added to the separatory funnel and the organic layer is separated from the inorganic layer.

The organic layer is washed with one liter of sodium carbonate and is then distilled on a 1" packed stone column yielding the following fractions:

| Fraction Number | Vapor Temp. (°C.) | Liquid Temp. (°C.) | Pressure mm/Hg |
|---|---|---|---|
| 1 | 25/20 | 18/20 | 10 |
| 2 | 80 | 90 | .2 |
| 3 | 81 | 92 | .2 |
| 4 | 83 | 96 | .2 |
| 5 | 81 | 130 | .2 |

| Fraction Number | Vapor Temp. (°C.) | Liquid Temp. (°C.) | Pressure mm/Hg |
|---|---|---|---|
| 6 | 80 | 200 | .2 |

The resulting product (bulked fractions 2–4) is analyzed by GLC, NMR and IR analysis to contain a mixture of compounds defined according to the structure:

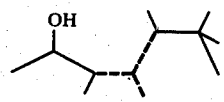

wherein in each of the compounds one of the dashed lines represents a carbon-carbon double bond and each of the other of the dashed lines represent carbon-carbon single bonds.

Fractions 2–6 have long lasting woody, amber, slightly fruity aroma and on dry-out have long-lasting vetiver nuances.

FIG. 9 is the GLC profile of the reaction product (conditions: 6'×¼" SF - 96 column programmed at 100°–120° C. at 8° C. per minute).

FIG. 10 is the infra red spectrum for the distillation product, bulked fractions 2–4.

EXAMPLE VI

PREPARATION OF DIISOAMYLENE ISOPROPYL CARBINOL

Reaction:

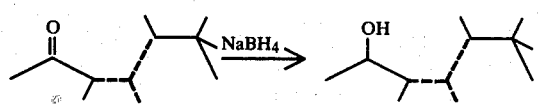

Into a 500 ml reaction flask equipped with reflux condenser, addition funnel, heating mantle, thermometer and nitrogen blanket provision is placed 210 grams of isobutyro diisoamylene prepared according to Example IV (bulked fractions 2–6). 18.7 grams of sodium borohydride is then dissolved in 100 ml ethanol. The resulting borohydride solution is then added to the isobutyro diisoamylene via the addition funnel while refluxing the reaction mass at 78°–80° C. over a 10 minute period. After addition of the sodium borohydride, the temperature of reaction mass is 80° C. The addition takes 10 minutes. The reaction mass is then heated at 65°–78° C. for an additional 12 hours after which period of time the reaction mass is transferred to a separatory funnel containing one liter of water. The organic phase is separated from the inorganic phase and the organic phase is washed with two additional one liter portions of water and is then distilled on a microvigreux column yielding the following fractions:

| Fraction Number | Vapor Temp. (°C.) | Liquid Temp. (°C.) | Pressure mm/Hg |
|---|---|---|---|
| 1 | 87/89 | 93/90 | 3/3 |
| 2 | 89 | 91 | 3 |
| 3 | 79 | 88 | 2.5 |
| 4 | 80 | 83 | 2 |
| 5 | 85 | 91 | 2 |

| Fraction Number | Vapor Temp. (°C.) | Liquid Temp. (°C.) | Pressure mm/Hg |
|---|---|---|---|
| 6 | 97 | 115 | 2 |
| 7 | 165 | 200 | 2 |

The resulting product has an intense, woody perfume aroma and a pleasant oriental/woody aroma in smoking tobacco both prior to and on smoking in the main stream and in the side stream.

FIG. 11 is the GLC profile for fraction 4 of the distillation product of the reaction product.

FIG. 12 is the infra red spectrum for the aforementioned reaction product subsequent to distillation (fraction 4).

FIG. 13 is the NMR spectrum for the aforementioned fraction 4 of the distillation product of the reaction product subsequent to distillation.

EXAMPLE VII

PERFUME FORMULATION

The following vetiver perfume formulation is prepared:

| Ingredients | Parts by Weight |
|---|---|
| Vetivone | 25 |
| Mixture of compounds defined according to the structure: 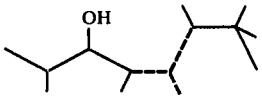 Prepared according to Example VI, fraction 4. | 12 |
| Mixture of compounds defined according to the structure: 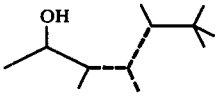 Prepared according to Example V, bulked fractions 2-4. | 12 |
| Vetiverol | 5 |
| Musk ketone | 8 |
| Styrax essence | 12.5 |

The addition of the mixture of secondary alcohols prepared according to Examples V and VI impart to this vetiver formulation intense woody, long-lasting aromas with fruity and powerful amber nuances.

EXAMPLE VIII

PERFUMED LIQUID DETERGENT

Concentrated liquid detergents with aromas as described in Table II below (which detergents are produced from the lysine salt of n-dodecyl benzene sulfonic acid as more specifically described in U.S. Pat. No. 3,948,818 issued on Apr. 6, 1976) are prepared containing one of the substances set forth in Table II below. They are prepared by adding and homogeneously mixing the appropriate quantity of substance as indicated in Table II below. The detergents all possess aroma profiles as set forth in Table II below, the intensity increasing with greater concentrations of the composition of matter as set forth in Table II below:

TABLE II

| Aroma Ingredient | Aroma Profile |
|---|---|
| Secondary alcohol mixture defined according to the structure: 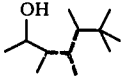 wherein one of the dashed lines represents a carbon-carbon double bond and each of the other of the dashed lines represent carbon-carbon single bonds, prepared according to Example V, fractions 2-4. | A fruity, amber, woody aroma with vetiver notes and having an intense vetiver aroma on dry-out. |
| Mixture of compounds defined according to the structure: 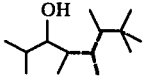 produced according to Example VI, fraction 4, wherein in each of the molecules of the mixture, one of the dashed lines represents a carbon-carbon double bond and each of the other of the dashed lines represent carbon-carbon single bonds. | An intense woody, long-lasting aroma with strong long-lasting vetiver nuances. |
| Perfume composition of Example VIII. | An intense vetiver aroma which is long-lasting containing woody, fruity and unusually powerful amber nuances. |

EXAMPLE IX

PREPARATION OF A COLOGNE AND HANDKERCHIEF PERFUME

Aroma imparting and augmenting ingredients as defined according to Table II in Example VIII are incorporated into colognes at concentrations of 1.5%, 2.0%, 2.5%, 3.0%, 4.0% and 5.0% in 75%, 80%, 80%, 90% and 95% solution of aqueous ethanol; and into handkercheif perfumes at concentration of 15%, 20%, 25% and 30% (in 80%, 85% and 95aqueous ethanol solutions). The use of the compositions of matter as set forth in Table II of Example VIII affords distinct and definitive aroma profiles as set forth in Table II of Example VIII to the handerchief perfumes and to the colognes.

EXAMPLE X

PREPARATION OF A SOAP COMPOSITION

One hundred grams of soap chips (IVORY ®) manufactured by the Procter & Gamble Company of Cincinnati, Oh., are melted and intimately admixed with one of the aroma materials as set forth in Table II of Examnple VIII supra, the amount of composition of matter of Table II of Example VIII being one gram of each composition of matter. The conditions of mixing are: 180° C, 3 hours, 12 atmospheres pressure. At the end of the mixing cycle, while the soap is still under 12 atmospheres pressure, the mixture of soap and perfume ingredient is cooled to room temperature. At this temperature, the resulting mixture is in a solid state. The resulting soap block is then cut up into soap cakes. Each of the soap cakes manifests an excellent aroma as set forth in Table II of Example VIII. None of the soap samples show any discoloration even after two weeks in the oven at 90° F.

EXAMPLE XI

PREPARATION OF A DETERGENT COMPOSITION

A total of 100 grams of a detergent powder (nonionic detergent powder containing a proteolytic enzyme prepared according to Example I of Canadian Pat. No. 985,190 issued on Mar. 9, 1976) is mixed with 0.15 grams of one of the compositions of matter as set forth in Table II of Example VIII until a substantially homogeneous composition is obtained. Each of the compositions has excellent aroma profiles as set forth in Table II of Example VIII.

EXAMPLE XII

PERFUMED LIQUID DETERGENTS

Concentrated liquid detergents with rich, pleasant aromas as set forth in Table II of Example VIII are prepared containing 0.10%, 0.15% and 0.20% of each of the compositions of matter set forth in Table II of Example VIII. They are prepared by adding and homogeneously admixing the appropriate quantity of composition of matter of Table II of Example VIII in the liquid detergent. The liquid detergents are all produced using anionic detergents containing a 50:50 mixture of sodium lauroyl sarcosinate and potassium N-methyl lauroyl tauride. The detergents all possess pleasant aromas as defined in Table II of Example VIII, the intensity increasing with greater concentrations of composition of matter of Table II of Example VIII.

EXAMPLE XIII

TOBACCO FORMULATION

A tobacco mixture is prepared by admixing the following ingredients:

| Ingredients | Parts by Weight |
|---|---|
| Bright | 40.1 |
| Burley | 24.9 |
| Maryland | 1.1 |
| Turkish | 11.6 |
| Stem (flue-cured) | 14.2 |
| Glycerine | 2.8 |
| Water | 5.3 |

Cigarettes are prepared from this tobacco.
The following flavor formulation is prepared:

| Ingredients | Parts by Weight |
|---|---|
| Ethyl butyrate | .05 |
| Ethyl valerate | .05 |
| Maltol | 2.00 |
| Cocoa extract | 26.00 |
| Coffee extract | 10.00 |
| Ethyl alcohol | 20.00 |
| Water | 41.90 |

The above stated tobacco flavor formulation is applied at the rate of 1.0% to all of the cigarettes produced using the above tobacco formulation. One-third of the cigarettes are then treated with 500 or 1000 ppm of the secondary alcohol mixture defined according to the structure:

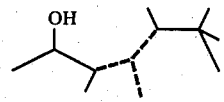

wherein in each of the molecules of the mixture, one of the dashed lines represents a carbon-carbon double bond and each of the other of the dashed lines represent carbon-carbon single bonds. Another third of the cigarettes are treated with 500 or 1000 ppm of the mixture produced according to Example VI defined according to the structure:

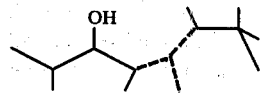

wherein in each of the molecules of the mixture, one of the dashed lines represents a carbon-carbon double bond and each of the other of the dashed lines represent carbon-carbon single bonds. The last third of the cigarettes are "control cigarettes" and do not contain any of the unsaturated alcohols of either Example V or Example VI but only contain untreated flavor formulation as set forth above. The control cigarettes and the treated experimental cigarettes are then evaluated by paired comparison and the results are as follows:

The experimental cigarettes are found to have more body and to be, on smoking, more Turkish tobacco-like, more aromatic and to have sweet, spicy, woody/oriental, minty and fruity aroma nuances in both the main stream and the side stream with additional clove-like nuances with respect to the composition of matter produced according to Example V. These aroma nuances are missing from the control cigarettes. The experimental cigarettes containing the composition of matter prepared according to Example V in the filter have a woody, tobacco character with heavy air-cured and cigar-like aroma nuances. The cigarettes containing the composition of matter of Example VI in the filter have sweet, minty aroma nuances both prior to and on smoking. The description can also be set forth as "menthol-like".

What is claimed is:

1. A process for augmenting or enhancing the aroma of a perfume composition or a cologne comprising the step of intimately admixing with a perfume composition or a cologne an aroma augmenting or enhancing quantity of at least one compound defined according to the structure:

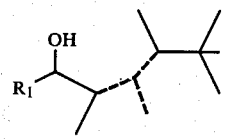

wherein R₁ is selected from the group consisting of methyl and isopropyl and wherein one of the dashed lines represents a carbon-carbon double bond and each of the other of the dashed lines represents carbon-carbon single bond.

2. A process for augmenting or enhancing the aroma of a perfume composition or cologne comprising the step of intimately admixing with a perfume composition or a cologne, a composition of matter which includes the compounds defined according to the structure:

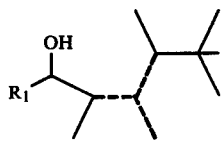

wherein R₁ represents methyl or isopropyl and in each of the molecules of the mixture, one of the dashed lines represents a carbon-carbon double bond and each of the other of the dashed lines represent carbon-carbon single bonds, produced according to a process comprising the step of intimately admixing a ketone having the structure:

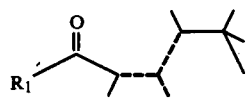

with a reducing agent selected from the group consisting of (i) an alkali metal boronhydride; (ii) lithium aluminum hydride and (iii) aluminum isopropylate and then fractionally distilling the resulting reaction mixture whereby a composition of matter consisting essentially of a material having the structure:

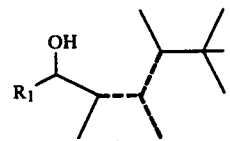

is produced.

* * * * *

UNITED STATES PATENT AND TRADEMARK OFFICE
CERTIFICATE OF CORRECTION

PATENT NO. : 4,336,164
DATED : June 22, 1982
INVENTOR(S) : RICHARD M. BODEN

It is certified that error appears in the above-identified patent and that said Letters Patent are hereby corrected as shown below:

Title page, left-hand column, line 7:

"Appl. No.: 252,134" should read

---Appl. No.: 252,334---

Signed and Sealed this

*Fourteenth* Day of *September 1982*

[SEAL]

*Attest:*

GERALD J. MOSSINGHOFF

*Attesting Officer*     *Commissioner of Patents and Trademarks*